US007183255B2

(12) United States Patent
Landry et al.

(10) Patent No.: US 7,183,255 B2
(45) Date of Patent: Feb. 27, 2007

(54) METHOD FOR STABILIZING BLOOD PRESSURE IN HEMODIALYSIS SUBJECTS

(75) Inventors: Donald W. Landry, New York, NY (US); Juan A. Oliver, New York, NY (US)

(73) Assignee: Intradialytic Pharmaceuticals, Niagara Falls, NY (US)

(*) Notice: Subject to any disclaimer, the term of this patent is extended or adjusted under 35 U.S.C. 154(b) by 0 days.

(21) Appl. No.: 10/789,548

(22) Filed: Feb. 26, 2004

(65) Prior Publication Data

US 2004/0229798 A1    Nov. 18, 2004

Related U.S. Application Data

(60) Provisional application No. 60/450,609, filed on Feb. 26, 2003.

(51) Int. Cl.
*A61K 38/17* (2006.01)
(52) U.S. Cl. .............................. 514/12; 514/2; 530/350
(58) Field of Classification Search ................ 514/12, 514/807; 530/315; 930/150
See application file for complete search history.

(56) References Cited

U.S. PATENT DOCUMENTS 5,906,974 A    5/1999  Blue et al.

FOREIGN PATENT DOCUMENTS

WO    WO 88/01163    * 2/1988

OTHER PUBLICATIONS

Lindberg et al. 1988, Lysine Vasopressin (LV) In The Treatment Of Refractory Hemodialysis Induced Hypotension (HIH), Kidney International, vol. 33, No. 1, p. 229.*
Lindberg et al. Kindey International, 1988, vol. 33, No. 1, p. 229.*
Dagher et al. Aliment Pharmacol. Ther., 2000, vol. 14. pp. 515-521.*
Jarcuska, P. et al., "Hemodialysis in Hepatorenal Syndrome Type 1 in Alcoholic Liver Cirrhosis Treated by Continual Terlipressin Infusion in Combination with Albumin Plasmaexpansion," *Journal of Hepatology*, 2003, 38:194-5, Abstract #675 (Exhibit 75).
Lindberg, Jill S. et al., "Lysine Vasopression (LV) in the Treatment of Refractory Hemodialysis Induced Hypotension (HIH)," *Kidney International*, 1988, 33:229 (Exhibit 76).
Landry, Donald W. et al., "Vasopressin Deficiency Contributes to the Vasodilation of Septic Shock," *Circulation*, 1997, 95:1122-5 (Exhibit 71).
Lilley, John J. et al., "Adrenergic Regulation of Blood Pressure in Chronic Renal Failure," *The Journal of Clinical Investigation*, 1976, 57:1190-200 (Exhibit 72).
Price, Michael R., "(Glyco-) protein antigens and peptide epitopes of tumours," *Tumour Immunobiology: A Practical Approach*, 1993, G. Gallagher et al. (eds.), pp. 63-79 (Exhibit 73).

Aisenbrey, Gary A. et al., "Vascular Effects of Arginine Vasopressin during Fluid Deprivation in the Rat," *The Journal of Clinical Investigation*, 1981, 67:961-8 (Exhibit 2).
Ardaillou, Raymond et al., "Secretion and Catabolism of Antidiuretic Hormone in Renal Failure," *Contributions to Nephrology*, 1986, 50:46-53 (Exhibit 3).
Argent, Nicholas B. et al., "Metabolic clearance rate of arginine vasopressin in severe chronic renal failure," *Clinical Science*, 1992, 83:583-7 (Exhibit 4).
Baldamus, C. A. et al., "Sympathetic and Hemodynamic Response to Volume Removal during Different Forms of Renal Replacement Therapy," *Nephron*, 1982, 31:324-32 (Exhibit 5).
Benmansour, Mustapha et al., "Metabolic clearance rate of immunoreactive vasopressin in man," *European Journal of Clinical Investigation*, 1982, 12:475-80 (Exhibit 6).
Blumberg, Alfred et al., "Extracellular Volume in Patients with Chronic Renal Disease Treated for Hypertension by Sodium Restriction," *The Lancet*, 1967, 2:69-73 (Exhibit 7).
Caillens, Henri et al., "Relationship between Change in Volemia at Constant Osmolality and Plasma Antidiuretic Hormone," *Mineral and Electrolyte Metabolism*, 1980, 4:161-71 (Exhibit 8).
Campese, Vito M. et al., "Mechanisms of autonomic nervous system dysfunction in uremia," *Kidney International*, 1981, 20:246-53 (Exhibit 9).
Charra, Bernard et al., "Control of Hypertension and Prolonged Survival on Maintenance Hemodialysis," *Nephron*, 1983, 33:96-9 (Exhibit 10).
Converse, Jr., Richard L. et al., "Paradoxical Withdrawal of Reflex Vasoconstriction as a Cause of Hemodialysis-induced Hypotension," *The Journal of Clinical Investigation*, 1992, 90:1657-65 (Exhibit 11).
D'Amore, T. Fasanella et al., "Response of plasma vasopressin to changes in extracellular volume and/or plasma osmolality in patients on maintenance hemodialysis," *Clinical Nephrology*, 1985, 23:299-302 (Exhibit 12).
Daul, Anton E. et al., "Arterial hypotension in chronic hemodialyzed patients," *Kidney International*, 1987, 32:728-35 (Exhibit 13).
Dunn, Fredrick L. et al., "The Role of Blood Osmolality and Volume in Regulating Vasopressin Secretion in the Rat," *The Journal of Clinical Investigation*, 1973, 52:3212-9 (Exhibit 14).
Endou, Kyoko et al., "Hemodynamic Changes during Hemodialysis," *Cardiology*, 1978, 63:175-87 (Exhibit 15).
Ewing, D. J. and R. Winney, "Autonomic Function in Patients with Chronic Renal Failure on Intermittent Haemodialysis," *Nephron*, 1975, 15:424-9 (Exhibit 16).

(Continued)

*Primary Examiner*—B. Dell Chism
(74) *Attorney, Agent, or Firm*—Mandel & Adriano

(57) ABSTRACT

The present invention provides a method for regulating blood pressure in a hemodialysis subject using a vasopressin receptor agonist, so as to facilitate removal of excessive extracellular fluid in the subject.

13 Claims, 11 Drawing Sheets

OTHER PUBLICATIONS

Fisch, Bruce J. and David M. Spiegel, "Assessment of excess fluid distribution in chronic hemodialysis patients using bioimpedance spectroscopy," *Kidney International*, 1996, 49:1105-9 (Exhibit 17).

Foley, Robert N. et al., "Impact of hypertension on cardiomyopathy, morbidity and mortality in end-stage renal disease," *Kidney International*, 1996, 49:1379-85 (Exhibit 18).

Friess, U. et al., "Failure of arginine-vasopressin and other pressor hormones to increase in severe recurrent dialysis hypotension," *Nephrology Dialysis Transplantation*, 1995, 10:1421-7 (Exhibit 19).

Graybiel, Ashton and R. Earle Glendy, "Circulatory Effects Following the Intravenous Administration of Pitressin in Normal Persons and in Patients with Hypertension and Angina Pectoris," *The American Heart Journal*, 1941, 21:481-9 (Exhibit 20).

Grollman, Arthur and E. M. K. Geiling, "The Cardiovascular and Metabolic Reactions of Man to the Intramuscular Injection of Posterior Pituitary Liquid (Pituitrin), Pitressin and Pitocin," *The Journal of Pharmacology & Experimental Therapeutics*, 1932, 46:447-60 (Exhibit 21).

Hegbrant, Jörgen et al., "Changes in Plasma Levels of Vasoactive Peptides during Standard Bicarbonate Hemodialysis," *Nephron*, 1993, 63:303-8 (Exhibit 22).

Hegbrant, Jörgen et al., "Changes in Plasma Levels of Vasoactive Peptides during Sequential Bicarbonate Hemodialysis," *Nephron*, 1993, 63:309-13 (Exhibit 23).

Heintz, B. et al., "Response of vasoactive substances to reduction of blood volume during hemodialysis in hypotensive patients," *Clinical Nephrology*, 1993, 39:198-204 (Exhibit 24).

Heintz, B. et al., "Response of Vasoactive Substances to Intermittent Ultrafiltration in Normotensive Hemodialysis Patients," *Nephron*, 1993, 65:266-72 (Exhibit 25).

Henderson, Lee W., "Symptomatic hypotension during hemodialysis," *Kidney International*, 1980, 17:571-6 (Exhibit 26).

Henrich, William L. et al., "Role of osmolality in blood pressure stability after dialysis and ultrafiltration," *Kidney International*, 1980, 18:480-8 (Exhibit 27).

Henrich, William L., "Hemodynamic instability during hemodiaylsis," *Kidney International*, 1986, 30:605-12 (Exhibit 28).

Horký, K. et al., "Plasma Concentration of Antidiuretic Hormone in Patients with Chronic Renal Insufficiency on Maintenance Dialysis," *Hormone and Metabolic Research*, 1979, 11:241-6 (Exhibit 29).

Iitake, Kazuhiro et al., "Effect of haemodialysis on plasma ADH levels, plasma renin activity and plasma aldosterone levels in patients with end-stage renal disease," *Acta Endocrinologica*, 1985, 110:207-13 (Exhibit 30).

Jaeger, Jack Q. and Ravindra L. Mehta, "Assessment of Dry Weight in Hemodialysis: An Overview," *Journal of American Society of Nephrology*, 1999, 10:392-403 (Exhibit 31).

Jawadi, M. Husain et al., "Regulation of Plasma Arginine Vasopressin in Patients with Chronic Renal Failure Maintained on Hemodialysis," *American Journal of Nephrology*, 1986, 6:175-81 (Exhibit 32).

Kaliszan, R. et al., "Constrictory Activity of Three New Arginine-Vasopressin (AVP) Analogues (ALA-AVP, SER-ALA-AVP, THR-SER-ALA-AVP) Towards Isolated Rat Tail Artery as Related to AVP Alone," *Pharmacological Research Communications*, 1988, 20:377-81 (Exhibit 33).

Katzarski, Krassimir S. et al., "A Critical Evaluation of Ultrasound Measurement of Inferior Vena Cava Diameter in Assessing Dry Weight in Normotensive and Hypertensive Hemodialysis Patients," *American Journal of Kidney Diseases*, 1997, 30:459-65 (Exhibit 34).

Kaufmann, Horacio et al., "Plasma endothelin during upright tilt: relevance for orthostatic hypotension?" *The Lancet*, 1991, 338:1542-5 (Exhibit 35).

Kersh, Edward S. et al., "Autonomic Insufficiency in Uremia as a Cause of Hemodialysis-Induced Hypotension," *The New England Journal of Medicine*, 1974, 290:650-3 (Exhibit 36).

Landry, Donald W. and Juan A. Oliver, "The Pathogenesis of Vasodilatory Shock," *The New England Journal of Medicine*, 2001, 345:588-95 (Exhibit 37).

Lazarus, J. Michael et al., "Hemodialysis," *The Kidney*, 1996, 5th ed., W.B. Saunders Co., Chapter 56, pp. 2424-2506 (Exhibit 38).

Leypoldt, John K. et al., "Relationship between volume status and blood pressure during chronic hemodialysis," *Kidney International*, 2002, 61:266-75 (Exhibit 39).

Mailloux, Lionel U. and William E. Haley, "Hypertension in the ESRD Patient: Pathophysiology, Therapy, Outcomes, and Future Directions," *American Journal of Kidney Diseases*, 1998, 32:705-19 (Exhibit 40).

Mallamaci, F. et al., "Autonomic function in uremic patients treated by hemodialysis or CAPD and in transplant patients," *Clinical Nephrology*, 1986, 25:175-80 (Exhibit 41).

Matsui, Kuniaki et al., "Effects of Nonhypotensive Hemorrhage on Renal Organ and Urinary Clearances of Vasopressin in the Dog," *Endocrinology*, 1983, 112:2114-9 (Exhibit 42).

Minaker, Kenneth L. et al., "Blood Pressure, Pulse, and Neurohumoral Responses to Nitroprusside-Induced Hypotension in Normotensive Aging Men," *The Journals of Gerontology*, 1991, 46:M151-4 (Exhibit 43).

Nakashima, Yoshiyuki et al., "Localization of Autonomic Nervous System Dysfunction in Dialysis Patients," *American Journal of Nephrology*, 1987, 7:375-81 (Exhibit 44).

Nakayama, Masaaki et al., "Stimulated Secretion of Arginine Vasopression during Hemodialysis in Patients with Hemodialysis Hypotension," *Nephron*, 1998, 79:488-9 (Exhibit 45).

Nies, Alan S. et al., "Hemodialysis hypotension is not the result of uremic peripheral autonomic neuropathy," *The Journal of Laboratory and Clinical Medicine*, 1979, 94:395-402 (Exhibit 46).

Padfield, P. L., "Changes of Vasopressin in Hypertension: Cause Or Effect?" *The Lancet*, 1976, 1:255-7 (Exhibit 47).

Pierratos, Andreas et al., "Nocturnal Hemodialysis: Three-Year Experience," *Journal of the American Society of Nephrology*, 1998, 9:859-68 (Exhibit 48).

Price, M. R. et al., "Epitope analysis of monoclonal antibody NCRC-11 defined antigen isolated from human ovarian and breast carcinomas," *British Journal of Cancer*, 1986, 54:393-400 (Exhibit 49).

Rosansky, S. J. et al., "Effect of osmolar changes on plasma arginine vasopressin (PAVP) in dialysis patients," *Clinical Nephrology*, 1991, 35:158-64 (Exhibit 50).

Rouby, Jean J. et al., "Hemodynamic changes induced by regular hemodialysis and sequential ultrafiltration hemodialysis: A comparative study," *Kidney International*, 17:801-10 (Exhibit 51).

Santoro, A. et al., "A Haemodynamic Study of Hypotension During Haemodialysis Using Electrical Bioimpedance Cardiography," *Nephrology Dialysis Transplantation*, 1990, 5(Suppl 1):147-53 (Exhibit 52).

Schwartz, Jeffrey and Ian A. Reid, "Effect of Vasopressin Blockade on Blood Pressure Regulation During Hemorrhage in Conscious Dogs," *Endocrinology*, 1981, 109:1778-80 (Exhibit 53).

Schwartz, Jeffrey et al., "Role of Vasopressin in Blood Pressure Regulation during Adrenal Insufficiency," *Endocrinology*, 1983, 112:234-8 (Exhibit 54).

Shade, R. E. and L. Share, "Metabolic Clearance of Immunoreactive Vasopressin and Immunoreactive [$^{131}$I]iodo Vasporessin in the Hypophysectomized Dog," *Endocrinology*, 1976, 99:1199-1206 (Exhibit 55).

Shaldon, S., "Progress from Haemodialysis," *Nephron*, 1981, 27:2-6 (Exhibit 56).

Shimamoto, Kazuaki et al., "A Study of Plasma Vasopressin in Patients Undergoing Chronic Hemodialysis," *Journal of Clinical Endocrinology & Metabolism*, 1977, 45:714-20 (Exhibit 57).

Shimamoto, Kazuaki et al., "Permeability of Antidiuretic Hormone and Other Hormones Through the Dialysis Membrane in Patients Undergoing Chronic Hemodialysis," *Journal of Clinical Endocrinology & Metabolism*, 1977, 45:818-20 (Exhibit 58).

Shiota, Jun et al., "Plasma Atrial Natriuretic Peptide during Hemodialysis with or without Fluid Removal," *Nephron*, 1990, 55:283-6 (Exhibit 59).

Sjöquist, P. O. B. et al., "Effect of a Vasopressin Analogue (N$^\alpha$-glycyl-glycyl-glycyl-[8-lysine]-vasopressin) on Organ Blood Flow in the Pregnant Guinea Pig," *Acta Pharmacologica et Toxicologica*, 1977, 40:369-77 (Exhibit 60).

Sjöquist, P.-O. B. et al., "Actions of a New Vasopressin Analogue (1-deamino-6-carba-[8-arginine]-vasopressin) on Regional Blood Flow in Pregnant Guinea Pigs," *Acta Pharmacologica et Toxicologica*, 1978, 43:190-5 (Exhibit 61).

Smith, Clark W. and Martha F. Ferger, "Synthesis and Some Pharmacological Properties of [3-β-(2-Thienyl)-L-alanine]-8-lysine-vasopressin," *Journal of Medicinal Chemistry*, 1975, 18:822-5 (Exhibit 62).

Spiegel, D. M. et al., "Bioimpedance resistance ratios for the evaluation of dry weight in hemodialysis," *Clinical Nephrology*, 2000, 53:108-14 (Exhibit 63).

Stone, William J. and Raymond M. Hakim, "Therapeutic Options in the Management of End-stage Renal Disease," *The Principles And Practice of Nephrology*, 1995, Chap. 95, pp. 650-654 (Exhibit 64).

Uusimaa, P. et al., "Neurohumoral responses to a single haemodialysis in chronic renal patients," *Acta Physiologica Scandinavica*, 1999, 165:25-31 (Exhibit 65).

Vertes, Victor et al., "Hypertension in End-Stage Renal Disease," *The New England Journal of Medicine*, 1969, 280:978-81 (Exhibit 66).

Wagner, Jr., Henry N. and Eugene Braunwald, "The Pressor Effect of the Antidiuretic Principle of the Posterior Pituitary in Orthostatic Hypotension," *The Journal of Clinical Investigation*, 1956, 35:1412-8 (Exhibit 67).

Weitzman, Richard E. et al., "Effect of osmolality on arginine vasopressin and renin release after hemorrhage," *American Journal of Physiology*, 1980, 238:E62-8 (Exhibit 68).

Zerbe, Robert L. et al., "Vasopressin Response to Orthostatic Hypotension," *The American Journal of Medicine*, 1983, 74:265-71 (Exhibit 69).

Ziegler, Michael G. et al., "Norepinephrine clearance, chromogranin A and dopamine β hydroxylase in renal failure," *Kidney International*, 1990, 37:1357-62 (Exhibit 70).

* cited by examiner

Greater Fluid Removal During HD by AVP Administration

| | Control | Vasopressin | |
|---|---|---|---|
| | Total Fluids | Total Fluids | Infusion Rate (mU kg$^{-1}$min$^{-1}$) |
| Patient 1 | 300cc NS | None | 0.15 |
| Patient 2 | 300cc NS | None | 0.15 |
| Patient 3 | 300cc NS, 250cc 5% Albumin, 100cc SPA | None | 0.15 |
| Patient 4 | 200cc NS | None | 0.30 |
| Patient 5 | None | None | 0.30 |

Figure 6

Greater Fluid Removal by Hemodialysis with AVP

The removal of 0.5 Kg extra fluid by hemodialysis was attempted in 10 patients, 5 of which received 0.3 mU/Kg/min AVP and the other 5 received placebo

- in the 5 patients on AVP, the blood pressure was stable and extra fluid removal was possible

- two of the 5 patients receiving placebo had an episode of low blood pressure that prevented the removal of extra fluid

Figure 7

METHOD FOR STABILIZING BLOOD PRESSURE IN HEMODIALYSIS SUBJECTS

This patent application claims the benefit of the filing date of U.S. Ser. No. 60/450,609, filed Feb. 26, 2003, the contents of all of the foregoing application are incorporated by reference in their entireties into the present patent application.

Throughout this application various publications are referenced. The disclosures of these publications in their entireties are hereby incorporated by reference into this application in order to more fully describe the state of the art to which this invention pertains.

FIELD OF THE INVENTION

The present invention provides methods for stabilizing blood pressure, e.g., high blood pressure, in a hemodialysis subject using a vasopressin receptor agonist, e.g., a V-1 receptor agonist.

BACKGROUND OF THE INVENTION

Hypertension is the leading cause of cardiovascular disease in patients on hemodialysis. A major contributor to hypertension in these patients is chronic volume expansion. Hemodialysis is often inadequate to remove all the excess fluid accumulated because of intradialytic hypotension, the most common acute complication of hemodialysis, occurring in 20–50% of all treatments (Bregman H, Daugirdas J T and Ing T S. in Handbook of Dialysis, second ed., Little, Brown and Co.(1994): chapter 9; Henrich, W L. Hemodynamic instability during hemodialysis. Kidney Int. (1986); 30: 605–612; Shaldon S. Progress from Haemodialysis. Nephron (1981); 27: 2–6; Lazarus J. M., Denker B. M., Owen W. F. in The Kidney, fifth ed., W. B. Sauders Company (1996): 56). Sequelae of intradialytic hypotension include general malaise, dizziness, muscle cramping, and vomiting, as well as the potentially lethal complications of myocardial ischemia and vomiting, as well as the potentially lethal complications of myocardial ischemia and cerebral hypoperfusion. In addition, hypotensive events impede the efficiency of fluid removal during the treatment. The primary cause of intradialytic hypotension is believed to be the rapid removal of intravascular volume (Bregman H, Daugirdas J T and Ing T S. in Handbook of Dialysis, second ed., Little, Brown and Co. (1994): chapter 9; Henrich, W L. Hemodynamic instability during hemodialysis. Kidney Int. (1986); 30: 605–612; Keshaviah, P., Jacobson, H. R., Striker G. E., Klahr S. in The. Principles and Practice of Nephrology, second ed., Mosby (1995): chapter 95), possibly exacerbated by a diminished baroreflex response (Campese V M, Romoff M S, Levitan D, Lane K and Massry S G. Kidney Int. (1981); 20: 246–253; Ziegler M G, Kennedy B, Morrissey E and O'Connor D T. Norepinephrine clearance, chromogranin A and dopamine beta hydoxylase in renal failure. Kidney Int. (1990); 37: 1357–1362; Kersh, E S, Kronfield S J, Unger A, Popper R W, Cantor S and Cohn K. Autonomic insufficiency in uremia as a cause of hemodialysis-induced hypotension. N. Eng. J. Med. (1974); 290: 650–653; Ewing D J and Winney R. Autonomic function in patients with chronic renal failure on intermittent hemodialysis. Nephron (1975); 15: 424–429; Lilley J J, Golden J and Stone R A. Adrenergic regulation of blood pressure in chronic renal failure. J. Clin. Invest. (1976); 57: 1190–1200; Nies A S, Robertson D and Stone W J. Hemodialysis hypotension is not the result of uremic peripheral neuropaihy. J. Lab. Clin. Med. (1979); 3: 395–402; Mallamaci C Z, Ciccarelli M and Briggs J D. Autonomic function in uremic patients treated by hemodialysis or CAPD and in transplant patients. Clin. Nephrol. (1986); 25: 175–180; Nakashima Y, Fetnat M F, Satoru N, Textor S C, Bravo E L and Tarazi R C. Localization of autonomic nervous system dysfunction in dialysis patients. Am. J. Nephrol. (1987); 7: 375–381; Daul A E, Wang X L, Miche M C and Brodde O. Arterial hypotension in chronic hemodialyzed patients. Kidney Int. (1987); 32: 728–735; Henrich W L. Hemodynamic instability during dialysis. Kidney Int. (1986); 30: 605–612).

Defense of blood pressure involves, in part, baroreflex-mediated autonomic afferent signaling to the posterior pituitary. This stimulatory signal causes a release of arginine vasopressin (AVP), which stimulates arterial smooth muscle to vasoconstrict. Two mechanisms appear to inhibit this pathway during hemodialysis: autonomic neuropathy and acute decreases in plasma osmolality. Autonomic neuropathy, a common co-morbid condition in many hemodialysis patients, can hinder the initial stimulatory signal for AVP secretion. The acute decrease in plasma osmolality that results from solute removal during hemodialysis directly inhibits AVP secretion. Therefore, it is our hypothesis that an AVP deficiency, due to an inappropriate decrease in secretion, contributes to the hypotensive episodes during hemodialysis. Although hypotension is a frequent complication on hemodialysis, hypertension is frequent between dialysis treatments. Chronic hypertension is a potent risk factor for cardiovascular morbidity and mortality. Cardiovascular mortality is the major contributor to the 40% five-year survival in ESRD patients.

The current treatment for intradialytic hypotension is volume infusion and/or a decrease in the rate of fluid removal. However, this solution abandons one of the principal objectives of hemodialysis, the removal of excess water ingested between treatments. The expedient of leaving patients with end-stage renal disease in a state of volume expansion in order to avoid intradialytic hypotension can cause or exacebate interdialytic hypertension. Ideally, treatment to facilitate dialytic fluid removal and ameliorate interdialytic hypertension would maintain blood pressure and permit adequate fluid removal. Exogenous AVP, a potential therapy for patients with a history of intradialytic hypotension, may diminish the number of hypotensive episodes and minimize the need for this expedient.

AVP is an intriguing hormone because it contributes little to blood pressure maintenance under normal conditions (Grollman A and Geiling E M K. J. Pharmacol. & Exper. Therap. (1932); 46: 447–460; Graybiel A and Glendy R E. Am. Heart J. (1941); 21: 481–489; Wagner H N and Braunwald E. J. Clin. Invest. (1956); 35: 1412–1418), but becomes critical when arterial pressure is threatened (Wagner H N and Braunwald E. J. Clin. Invest. (1956); 35: 1412–1418 Aisenbrey G A, Handelman W A, Arnold O, Manning M and Schrier R W. J. Clin. Invest. (1981); 67: 961–968; Schwartz J and Reid I A. Endocrinology (1981); 108: 1778–1780; Schwartz J, Keil L C, Maselli J and Reid I A. Endocrinology (1983); 112: 234–238). When AVP fails to be secreted by bororeflex-mediated stimulation, hypotension and inappropriate vasodilation ensue. This most commonly occurs in the setting of autonomic neuropathy, where we (Kaufmann H, Oribe E and Oliver J A. Plasma endothelin during upright tilt: relevance for orthostatic hypotension? Lancet (1991); 338: pp. 1542–45) and others (Zerbe R L, Henry D P and Robertson G L. Vasopressin response to orthostatic hypotension. Etiologic and clinical implications. Am. J. Med. (1983); 74: pp. 265–271) have shown that hypotension fails to induce AVP secretion. Recently, we have also found that septic shock is characterized by a defect in bororeceptor reflex-mediated secretion of AVP (Landry D W, Levin H R, Gallant E M, Ashton R C, Seo S, D'Allesandro D, Oz, M C and Oliver J A. Vasopressin deficiency contributes to the vasodilation of septic shock. Circ. (1997); 95: pp 1122–1125).

AVP hypersensitivity has been reported in the setting of autonomic neuropathy, and we have recently demonstrated that AVP deficiency and hypersensitivity also characterize vasodilatory septic shock (Landry D W, Levin H R, Gallant E M, Ashton R C, Seo S, D'Alessandro D, Oz M C and Oliver J A). Vasopressin deficiency contributes to the vasodilation of septic shock. Circ. (1997); 95: 1122–1125). These observations suggest that hypotensive episodes associated with AVP deficiency are likely to respond to very low doses of exogenous hormone.

Secretion of AVP is Defective in Hemodialysis Patients

AVP is released from the posterior pituitary through activation of the baroreflex by a decrease in arterial pressure or through activation of hypothalamic osmoreceptors by a rise in serum osmolality. A large body of evidence suggests that both stimuli of AVP secretion are compromised during dialysis.

Autonomic Dysfunction

Autonomic neuropathy is a common co-morbid condition in patients with renal failure requiring dialysis (Campese V M, Romoff M S, Levitan D, Lane K and Massry S G. Kidney Int. (1981); 20: 246–253; Ziegler M G, Kennedy B, Morrissey E and O'Connor D T. Norepinephrine clearance, chromogranin A and dopamine beta hydoxylase in renal failure. Kidney Int. (1990); 37: 1357–1362; Kersh, E S, Kronfield S J, Unger A, Popper R W, Cantor S and Cohn K. Autonomic insufficiency in uremia as a cause of hemodialysis-induced hypotension. N. Eng. J. Med. (1974); 290: 650–653; Ewing D J and Winney R. Autonomic function in patients with chronic renal failure on intermittent hemodialysis. Nephron (1975); 15: 424–429; Lilley J J, Golden J and Stone R A. Adrenergic regulation of blood pressure in chronic renal failure. J. Clin. Invest. (1976); 57: 1190–1200; Nies A S, Robertson D and Stone W J. Hemodialysis hypotension is not the result of uremic peripheral neuropathy. J. Lab. Clin. Med. (1979); 3: 395–402; Mallamaci C Z, Ciccarelli M and Briggs J D. Autonomic function in uremic patients treated by hemodialysis or CAPD and in transplant patients. Clin. Nephrol. (1986); 25: 175–180; Nakashima Y, Fetnat M F, Satoru N, Textor S C, Bravo E L and Tarazi R C. Localization of autonomic nervous system dysfunction in dialysis patients. Am. J. Nephrol. (1987); 7: 375–381; Daul A E, Wang X L, Miche M C and Brodde O. Arterial hypotension in chronic hemodialyzed patients. Kidney Int. (1987); 32: 728–735; Henrich W L. Hemodynamic instability during dialysis. Kidney Int. (1986); 30: 605–612). In fact, 37% of patients on hemodialysis in the USA have diabetes mellitus, a disease in which one of the major manifestations is autonomic neuropathy. As baroreflex-mediated secretion requires intact autonomic afferent pathways, many patients on hemodialysis may have insufficient AVP release in response to decreased circulating blood volume.

Hypo-osmolality

Patients with end-stage renal disease generally demonstrate a baseline hyperosmolality in their intra- and extracellular copmpartments. Hemodialysis causes a rapid fall in plasma osmolality, which can suppress AVP secretion even in the setting of hypovolemia. In fact, there are significant data showing that plasma AVP levels decrease or remain unchanged during dialysis despite decreases in blood pressure due to fluid removal (Hegbrandt J, Thysell J, Martensson L, Ekman R and Boberg U. Changes in plasma levels of vasoactive peptides during sequential bicarbonate hemodialysis. Nephron (1993); 63: 309–313; Shimamoto K, Ikuo W and Miyahara M. A study of plasma vasopressin in patients undergoing chronic hemodialysis. J. Clin. Endocrin. Met. (1977); 45: 714–720; Horky K, Sramkova J, Lachmanova J, Tomasek R and Dvorakova J. Plasma concentration of antidiuretic hormone in patients with chronic renal insufficiency on maintenance dialysis. Horm. Metab. Res. (1979); 11: 241–246; Caillens H, Prusczynski W, Neyrier A, Ang K, Rousselet F and Ardaillou R. Relationship between change in volemia at constant osmolality and plasma antidiuretic hormone. Miner. Electrolyte Metab. (1980); 4: 161–171; D'Amore T F, Wauters J P, Waeber B, Nussberger J and Brunner H R. Response of plasma vasopressin to changes in extracellular volume and/or osmolality in patients on maintenance hemodialysis. Clin. Nephrol. (1985); 23: 299–302; Iitake K, Kimura T, Matsui K, Ota K, Masaru S, Inoue M and Yoshinaga K. Effect of hemodialysis on plasma ADH levels, plasma renin activity and plasma aldosterone levels, in patients with end-stage renal disease. Acta Endocrin. (1985); 110: 207–213; Jawadi M H, Ho L S, Dipette D and Ross D L. Regulation of plasma arginine vasopressin in patients with chronic renal failure maintained on hemodialysis. Am. J. Nephrol. (1986); 6: 175–181; Rosansky S J, Rhinehart R and Shade R. Effect of osmolar changes on plasma arginine vasopressin (PAVP) in dialysis patients. Clin. Nephrol. (1991); 35: 158–164; Shiota J, Kubota M, Hamada C and Koide J. Plasma atrial natriuretic peptide during hemodialysis with or without fluid removal. Nephron (1990); 55: 283–286; Hegbrandt J, Thysell J, Martensson L, Ekman R and Boberg U. Changes in plasma levels of vasoactive peptides during standard bicarbonate hemodialysis. Nephron (1993); 63: 303–308). Moreover, it has long been known that intravenous infusion of hyperosmotic solutions, such as mannitol or hypertonic saline, greatly ameliorates intradialytic hypotension (Henrich W L, Woodard T D, Blachley J D, Gomez-Sanchez C, Pettinger W and Cronin R E. Role of osmolality in blood pressure stability after dialysis and ultrafiltration. Kidney Int. (1980); 18: 480–488), possibly by facilitating AVP secretion in addition to augmenting circulating volume.

SUMMARY OF INVENTION

The present invention provides a rational method for reducing excess extracellular fluid in a subject undergoing hemodialysis by administering a vasopressin receptor agonist (e.g., a V-1 receptor agonist, e.g., a V1a receptor agonist) to the subject in an effective amount and thereby maintaining blood pressure during hemodialysis in order to facilitate reducing excess extracellular fluid in the subject.

The invention further provides a method for stabilizing blood pressure, e.g., high blood pressure, between hemodialysis treatments in a subject undergoing renal replacement therapy, e.g., undergoing a hemodialysis treatment by administering a vasopressin receptor agonist (e.g., a V-1 receptor agonist, e.g., a V1a receptor agonist) to the subject.

The invention further provides a method for inhibiting intradialytic hypotension in a subject by regulating blood pressure by administering a vasopressin receptor agonist (e.g., a V-1 receptor agonist, e.g., a V1a receptor agonist) to the subject.

The invention further provides a method for inhibiting interdialytic hypertension in a subject by regulating blood pressure by administering a vasopressin receptor agonist (e.g., a V-1 receptor agonist, e.g., a V1a receptor agonist) to the subject undergoing renal replacement therapy, e.g., undergoing a hemodialysis treatment.

BRIEF DESCRIPTION OF DRAWINGS

FIG. 6 depicts greater fluid removal during hemodialysis by AVP administration. In the five patients on AVP, the blood pressure was stable and extra fluid removal was possible. In 4/5 of the control patients, extra fluid had to be administered.

FIG. 7 depicts greater fluid removal by hemodialysis with AVP. In the group of patients receiving placebo, two patients had an episode of low blood pressure that prevented the removal of extra fluid.

DETAILED DESCRIPTION OF THE INVENTION

Definitions

Figure 1:
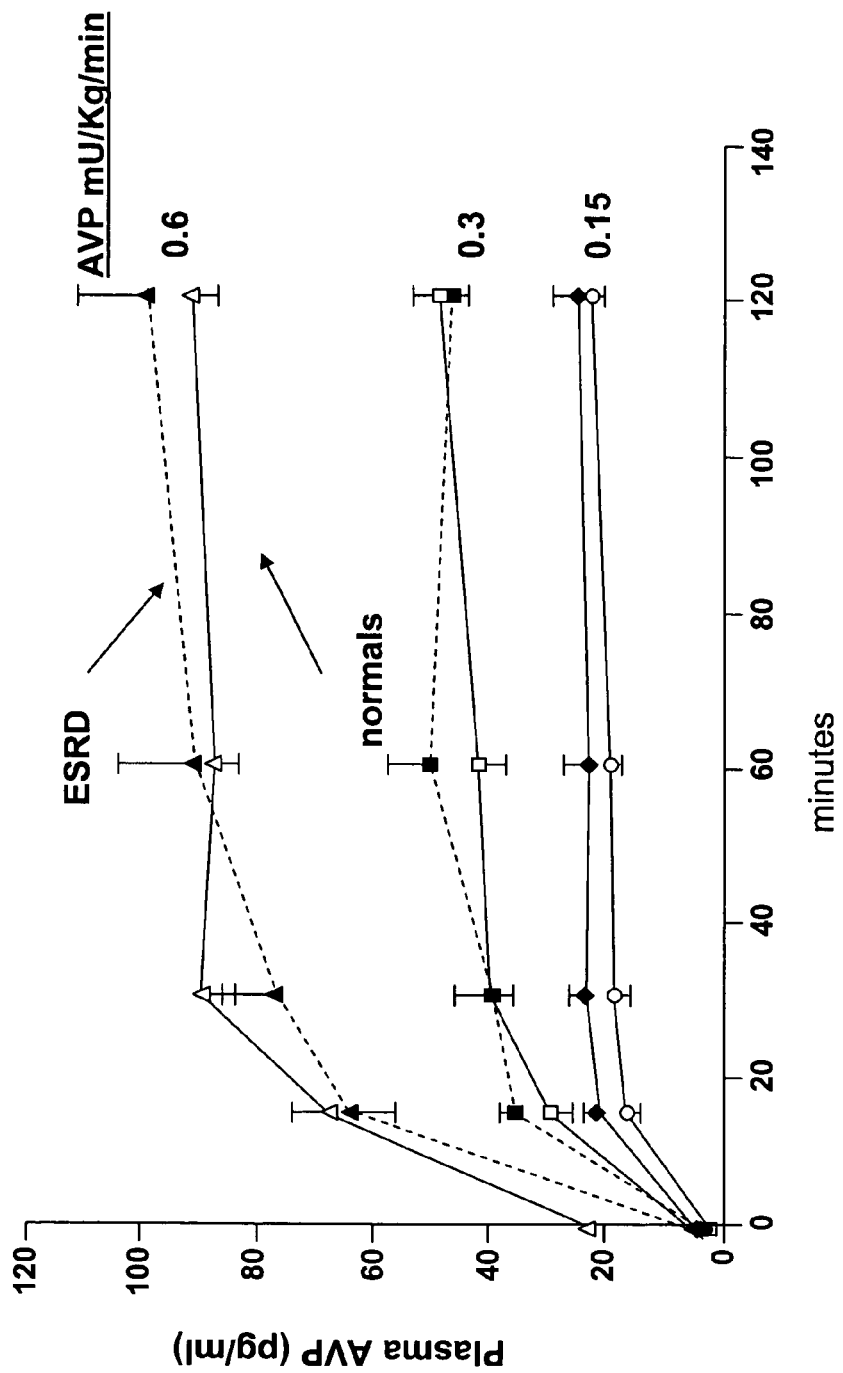
FIG. 1 depicts that normal subjects (straight lines) and patients with end-stage renal failure (broken lines) handle exogenous AVP identically. When given at 0.15, 0.3 or 0.6 mU/Kg/min, the plasma concentrations of AVP were identical.

As used in this application, the following words or phrases have the meanings specified.

As used herein, the term "V-1 receptor agonist" refers to a molecule that activates a V-1 receptor in the vascular smooth muscle cells, thereby constricting the blood vessels and raising the blood pressure.

As used herein, the term "V-1 receptor" refers to specific molecular site(s) or structure(s) on or in cells that vasopressin binds to so as to modify the function of cells. The V-1 receptor can be subdivided into V1a and V1b (formerly V3) receptors.

As used herein, the term "inhibiting hypotension" refers to maintaining systolic blood pressure above 90 mm Hg or not more than 40 mm Hg below a patient's baseline blood pressure.

As used herein "inhibiting hypertension" refers to maintaining systolic blood pressure less than 140 mm Hg or reducing systolic blood pressure by more than 5 mm Hg.

As used herein, "subject," is used in its broadest sense. A subject includes a human, non-human primate, rabbit, sheep, rat, dog, cat, pig, or mouse.

In order that the invention herein described may be more fully understood, the following description is set forth.

The present invention provides methods for reducing excess extracellular fluid in a subject undergoing renal replacement therapy, e.g., undergoing a hemodialysis treatment, by administering a vasopressin receptor agonist (e.g., a V-1 receptor agonist, e.g., a V1a receptor agonist) to the subject in an effective amount and thereby maintaining blood pressure during hemodialysis in order to facilitate reducing excess extracellular fluid in the subject. In accord with the invention, administration may be effected before, during and/or after the hemodialysis treatment. Hemodialysis includes all of the dialytic modalities used to treat renal failure including hemodialysis, hemofiltration, and hemodiafiltration.

The invention further provides a method for stabilizing blood pressure, e.g., high blood pressure, between hemodialysis treatments in a subject undergoing renal replacement therapy, e.g., undergoing a hemodialysis treatment, by reducing excess extracellular by administering a vasopressin receptor agonist to the subject (e.g., a V-1 receptor agonist, e.g., a V1a receptor agonist).

The invention further provides a method for inhibiting intradialytic hypotension in a subject by regulating blood pressure by administering a vasopressin receptor agonist to the subject undergoing renal replacement therapy, e.g., undergoing a hemodialysis treatment.

The invention further provides a method for inhibiting interdialytic hypertension in a subject by regulating blood pressure by administering a vasopressin receptor agonist to the subject.

The examples of vasopressin receptor agonist that can increase blood pressure include but are not limited to arginine vasopressin, lysine vasopressin, triglycil-lysine vasopressin (glycopressin) (also known as TERLIPRESSIN), octopressin, and ornipressin.

Additionally analogs of arginine vasopressin including but not limited to analogues extended by 1–3 amino acids such as Ala-AVP, Ser-Ala-AVP, Thr-Ser-Ala-AVP (Kaliszan R, Petrusewicz J, Juzwa W, Rekowski P, Lammek B, Kupryszewski G. *Pharmacol Res Commun* 1988 May;20 (5):377–81) may be used.

Additional examples of vasopressin-receptor agonists include organic compounds that have the ability to bind and activate the vasopressin receptor for vasopressin which is present in vascular smooth muscle cells. These compounds can induce muscle (and blood vessel) constriction and increase the blood pressure. Examples of these compounds include but are not limited to 3-beta-(2-thienyl)-L-alanine)-8-lysine-vasopressin (Smith C W, Ferger M F, Chan W Y, J Med Chem 1975 August;18(8):822–5); N-alpha-glycyl-glycyl-glycyl-[8-lysine]-vasopressin (Sjoquist P O, Bjellin L, Carter A M., Acta Pharmacol Toxicol (Copenh) 1977 March; 40(3):369–77); and 1-deamino-6-carba-[8-arginine]-vasopressin (Sjoquist P O, Martensson L, Bjellin L, Carter A M., Acta Pharmacol Toxicol (Copenh) 1978 September;43(3): 190–5, and analogs thereof.

In addition to the specific vasopressin receptor agonist molecules identified herein for use in the methods of the invention, other vasopressin receptor agonist molecules may be suitable in the methods of the invention and such molecules can be identified using standard techniques such as binding assays. For example, any of the molecules of the invention (e.g. arginine vasopressin, lysine vasopressin, triglycil-lysine vasopressin (glycopressin), octopressin, and ornipressin) can be used to screen for other suitable molecules including libraries of small molecules in any of a variety of screening techniques. The molecules of the invention employed in such screening may be free in solution, affixed to a solid support, or borne on a cell surface. The formation of binding complexes, between any of the molecules of the invention and the agent being tested, may be measured (e.g. published PCT application WO84/03564; Price, M. R.,et al. 1986. Br. J. Cancer 54:393 (88); Gallegher, G., et al, 1993. Tumour Immunobiology, pages 63–79, Oxford University Press Inc., New York (89)).

In accord with the methods of the invention, vasopressin receptor agonist molecules of the invention can be used alone or in combination with another vasopressin receptor agonist molecule (e.g., two or more vasopressin receptor agonist molecules can be administered). In an additional embodiment, the method further comprising administering a second agent or drug commonly used during renal replacement therapy.

A vasopressin receptor agonist of the invention may be administered to a subject in an effective amount to achieve a steady state concentration of e.g. 30–100 pg/ml, which may be an appropriate range of serum AVP in normal patients responding to acute hypotension. The vasopressin receptor agonist of the invention can be administered to a subject in a range of e.g., about 0.01 milliunits/kg/minute-2.0 milliunits/kg/hr.

In preferred embodiments, the effective amount of a vasopressin receptor agonist is about 0.15 milliunits/kg/minute to 0.60 milliunits/kg/minute.

Agonist molecules useful in the methods of the invention identified herein, as well as other molecules identified by e.g. screening assays, can be administered for the treatment of various disorders as noted above and below in the form of pharmaceutical compositions. The pharmaceutical compositions may also contain one or more of the vasopressin agonist molecules useful in the methods of the invention or may also contain, in addition to the vasopressin agonist molecules, other drugs necessary for the particular indication being treated, preferably those with complementary activities that do not adversely affect each other. Alternatively, or in addition, the composition may comprise an agent that enhances the function of the receptor agonist molecules. Such molecules are suitably present in combination in amounts that are effective for the purpose intended.

In a further embodiment of the invention, there are provided articles of manufacture and kits containing vasopressin receptor (VR) agonist(s) which can be used, for instance, for the therapeutic or non-therapeutic applications described herein. The article of manufacture comprises a container with a label. Suitable containers include, for example, bottles, vials, and test tubes. The containers may be formed from a variety of materials such as glass or plastic. The container holds a composition which includes an active agent that is effective for therapeutic or non-therapeutic applications, such as described above. The active agent in the composition is a VR agonist (e.g., a VR-1 agonist). The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

The agonist molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the severity and course of the disease, the subject's health and response to treatment and the judgment of the treating physician. Accordingly, the dosages of the molecules should be titrated to the individual subject.

EXAMPLES

The following examples are presented to illustrate the present invention and to assist one of ordinary skill in making and using the same. The methodology and results may vary depending on the intended goal of treatment and the procedures employed. The examples are not intended in any way to otherwise limit the scope of the invention.

Example 1

This Example describes the procedure to utilize vasopressin to stabilize blood pressure during hemodialysis and facilitate removal of excess extracellular fluid.

Description of Study Procedures

Healthy controls and patients with end-stage renal disease (e.g. defined as creatinine clearance of less than 10 ml/min) were studied. The studies were conducted on regularly scheduled hemodialysis days. The duration of hemodialysis remained the same as that prescribed prior to the study period. AVP or placebo (normal saline) was administered at a constant rate of 0.15, 0.3 or o.6 mU/kg/min through a venous line (controls) or through the venous limb of the dialysis circuit (hemodialysis patients). The patient's hemodialysis prescription remained unchanged except for the administration of AVP or placebo. Intradialytic hypotension was treated in the customary manner with the infusion of isotonic and hypertonic fluids.

Serum AVP levels were determined by a radioimmunoassay technique. Blood pressure was measured with a cuff-type sphygmomanometer at 20 minute intervals.

In an embodiment, the following protocol can be used:

1) Prior to the first session of dialysis under study, a medical evaluation is performed. This evaluation includes a baseline EKG, if one has not been, performed within the last three months.

2) A polysulfone dialysis membrane appropriate to each patient's weight is selected.

3) The dialysate sodium concentration is preferably about 140 mEq/L.

4) Following routine protocol, weight was recorded before and after hemodialysis.

5) At the initiation of dialysis, AVP or placebo (identity unknown to investigators, dialysis staff and patient) is infused through the venous (blood return) limb of the dialysis circuit for the duration of the dialysis session. AVP can be administered at an infusion rate of 0.3 mU kg$^{-1}$min$^{-1}$ for the duration of the dialysis session.

6) During dialysis, blood pressure and heart rate is preferably recorded every 15 minutes.

7) The type and volume of fluids infused during hemodialysis can be recorded.

8) Hypotensive episodes may be treated in the customary fashion with administration of fluids and/or a decrease in the rate of fluid removal.

9) At the end of the treatment session, patients can be asked to complete a questionnaire detailing severity and frequency of intradialytic symptoms of hypovolemia (headache, dizziness, nausea, vomiting and cramping). At the initiation of the next treatment session, patients were asked about symptoms during the 12-hour period following treatment.

Results

AVP Levels are Suppressed During Dialysis.

Solute removal during hemodialysis, which decreases plasma osmolality, can directly inhibit AVP secretion. Indeed, we found that plasma AVP in ten patients during hemodialysis failed to significantly increase despite that both blood pressure and extracellular fluid volume decreased (3.1 pg/ml before dialysis and 5.1 pg/ml at 3 h of treatment; p=ns).

1) n=10; Mean AVP Plasma Concentration and Systolic Arterial Pressure

| Min | [AVP] | SBP (mm Hg) |
|---|---|---|
| 0 | 3.1 pg/ml | 144 ± 20 (SD) |
| 60 | 2.3 | 132 ± 19 |
| 120 | 4.1 | 131 ± 23 |
| 180 | 5.0 | 132 ± 31 |

Analysis of variance showed that whereas time on dialysis had no effect on the AVP plasma concentration, it had a significant effect on the systolic arterial pressure (p<0.01). In other words, while systolic arterial pressure fell during hemodialysis, plasma AVP did not change. In as much as a lowering of the blood pressure is a potent stimulus for AVP secretion, these results indicated that patients with ESRD have a deficiency on AVP secretion during dialysis.

We conducted a study of AVP pharmacokinetics in healthy control subjects and hemodialysis patients. Hemodialysis patients and control subjects achieved similar serum concentrations of AVP during constant infusion (FIG. 1). Thus, the presumed AVP deficiency was probably not related to altered metabolism of AVP in hemodialysis patients or to clearance of AVP from the circulation via the hemodialysis membrane employed in our study. We therefore concluded that AVP secretion may be inappropriately suppressed during episodes of intradialytic hypotension, due to the effects of autonomic dysfunction or relative hypo-osmolality as described above.

Plasma AVP is not dialyzed. To examine whether administration of exogenous AVP could prevent intradialytic hypotension, it was first determined whether the dialysis procedure removed the hormone from the blood. To determine this, AVP was administered at doses that had no effect in normal subjects and determined the plasma concentrations and pressure responses to AVP infusion in healthy control subjects and hemodialysis patients. Hemodialysis patients and control subjects achieved similar serum concentrations of AVP; infusion of 0.3 mU/kg/min resulted in a plasma level of ~40 pg/m, a concentration which occurs physiologically during acute hypotension. Insitution of HD during constant AVP infusion did not decrease AVP plasma levels. Thus, HD does not clear the hormone from the blood.

To rule out the possibility that the lack of a rise in plasma AVP during dialysis was due to the fact that the newly secreted hormone was being dialyzed as was being secreted, we measured plasma AVP during the infusion of exogenous AVP to ERDS patients during control conditions and during hemodialysis.

As shown, during the constant infusion of 0.15, 0.3 and 0.6 g/min, the plasma concentrations at 2 h were found to be not significantly different during control and dialysis periods:

| n | dose | control | hemodialysis |
|---|---|---|---|
| 4 | 0.15 | 25.7 | 28.9 |
| 4 | 0.3 | 47.4 | 51.2 |
| 4 | 0.6 | 100.0 | 104.6 |

Figure 2:
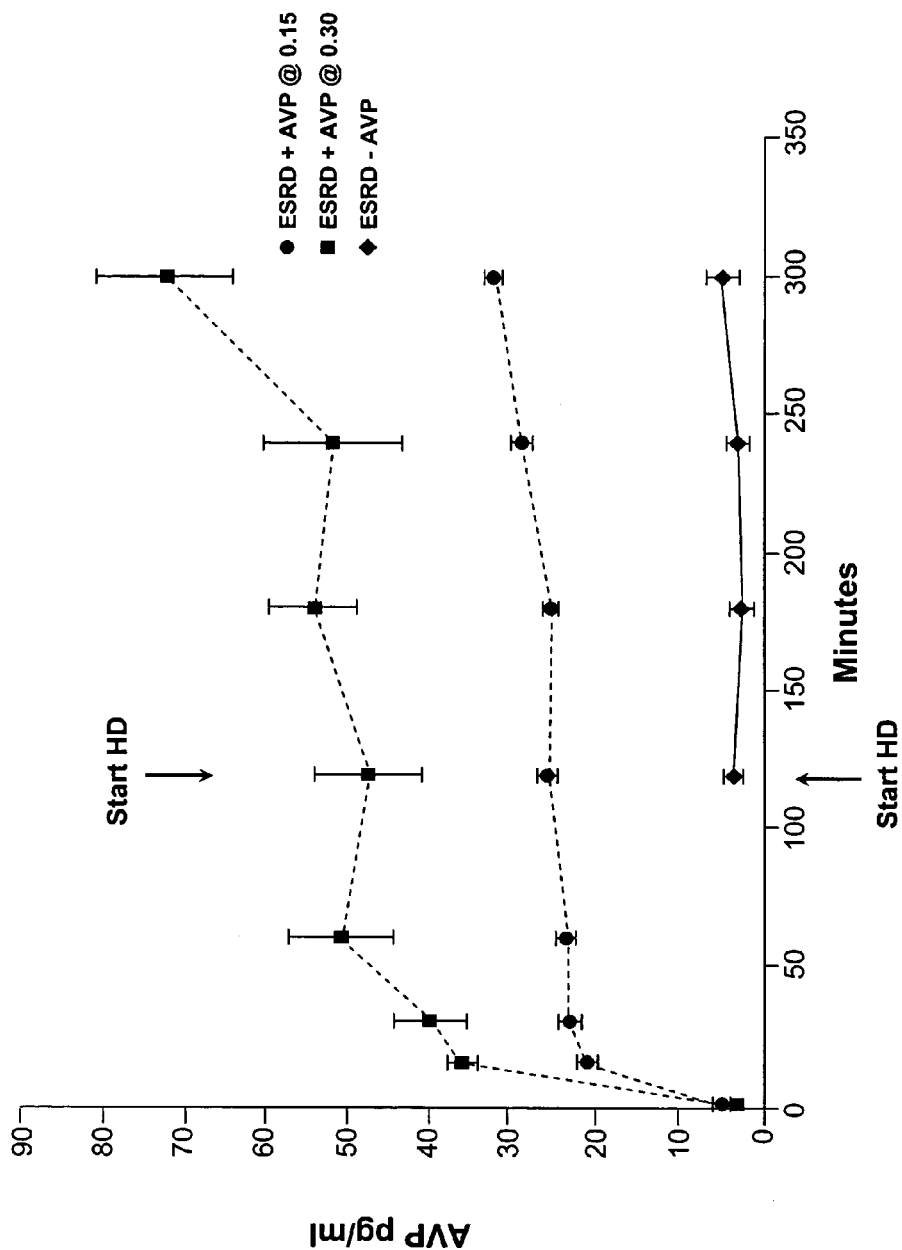
FIG. 2 depicts that during constant AVP infusion of either 0.15 or 0.3 mU/Kg/min, plasma AVP did not significantly change when hemodialysis (HD) was started. The figure also shows that endogenous plasma AVP (solid line) does not increase during HD.

As shown in FIG. 2, during constant AVP infusion of either 0.15 or 0.3 mU/kg/min, plasma AVP did not change significantly when hemodialysis was started. The figure also shows that endogenous plasma AVP does not increase during hemodialysis.

In conclusion, plasma vasopressin is not dialyzed or more quickly metabolized during hemodialysis and the lack of a significant increase in its concentration during hemodialysis despite that the blood pressure falls can be attributed to impaired secretion.

Exogenous AVP increases blood pressure in patients with end-stage renal failure. We discovered that patients with ERSD are hypersensitive to vasopressin's pressor action. BP rose significantly when AVP was infused, at doses without a pressor effect in normal subjects, into end-stage renal failure patients who were not on dialysis, not in shock and without idiopathic orthostatic hypotension (primary autonomic neuropathy).

The administration of exogenous AVP to patients with ESDR led to the discovery that these patients are hyper-responsive to the vascular effect of this hormone. As shown, we found that the doses of hormone given, while unable to increase pressure in normal subjects, had a significant pressor action in patients with ERSD.

| Group | n | before | Minutes of infusion | | | |
|---|---|---|---|---|---|---|
| | | | 30 | 60 | 90 | 120 |
| normals | 12 | 115 ± 13 | 114 ± 10 | 113 ± 10 | 114 ± 10 | 113 ± 11 |
| ESRD | 12 | 153 ± 28 | 162 ± 30 | 161 ± 32 | 161 ± 28 | 150 ± 31 | all values are M ± SD; response of the two groups to AVP was significantly different (p < 0.02) by ANOVA.

all values are M±SD; response of the two groups to AVP was significantly different (p<0.02) by ANOVA.

Figure 3A:
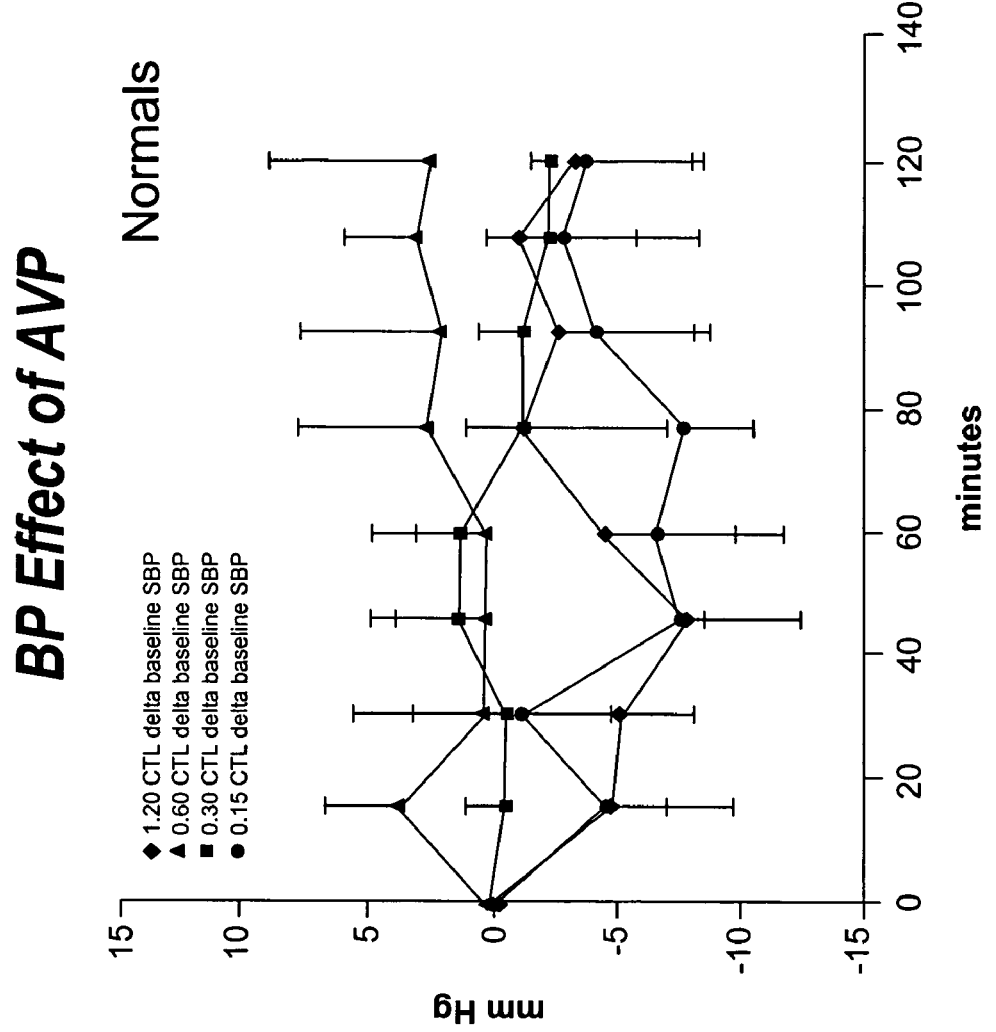
FIG. 3 depicts that the same dose of AVP has no pressure action in normal subjects but increases blood pressure in patients with renal failure (end-stage renal disease; ESRD). That is, these patients are hypersensitive to AVP.
Figure 3B:
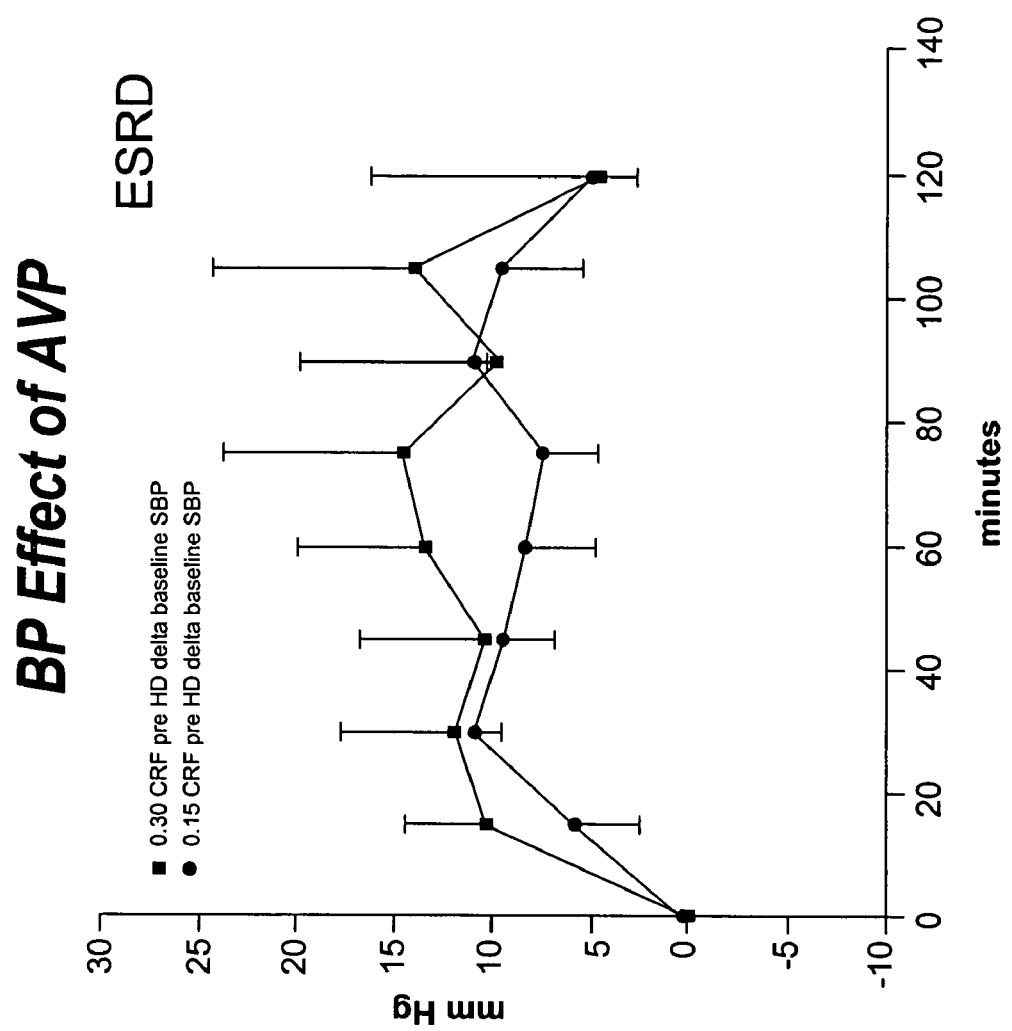

Administration of same dose of AVP had no pressure action in normal subjects (FIG. 3A), but increased systolic arterial blood pressure in patients with end-stage renal disease (FIG. 3B), suggesting that these patients are hypersensitive to AVP.

Figure 4:
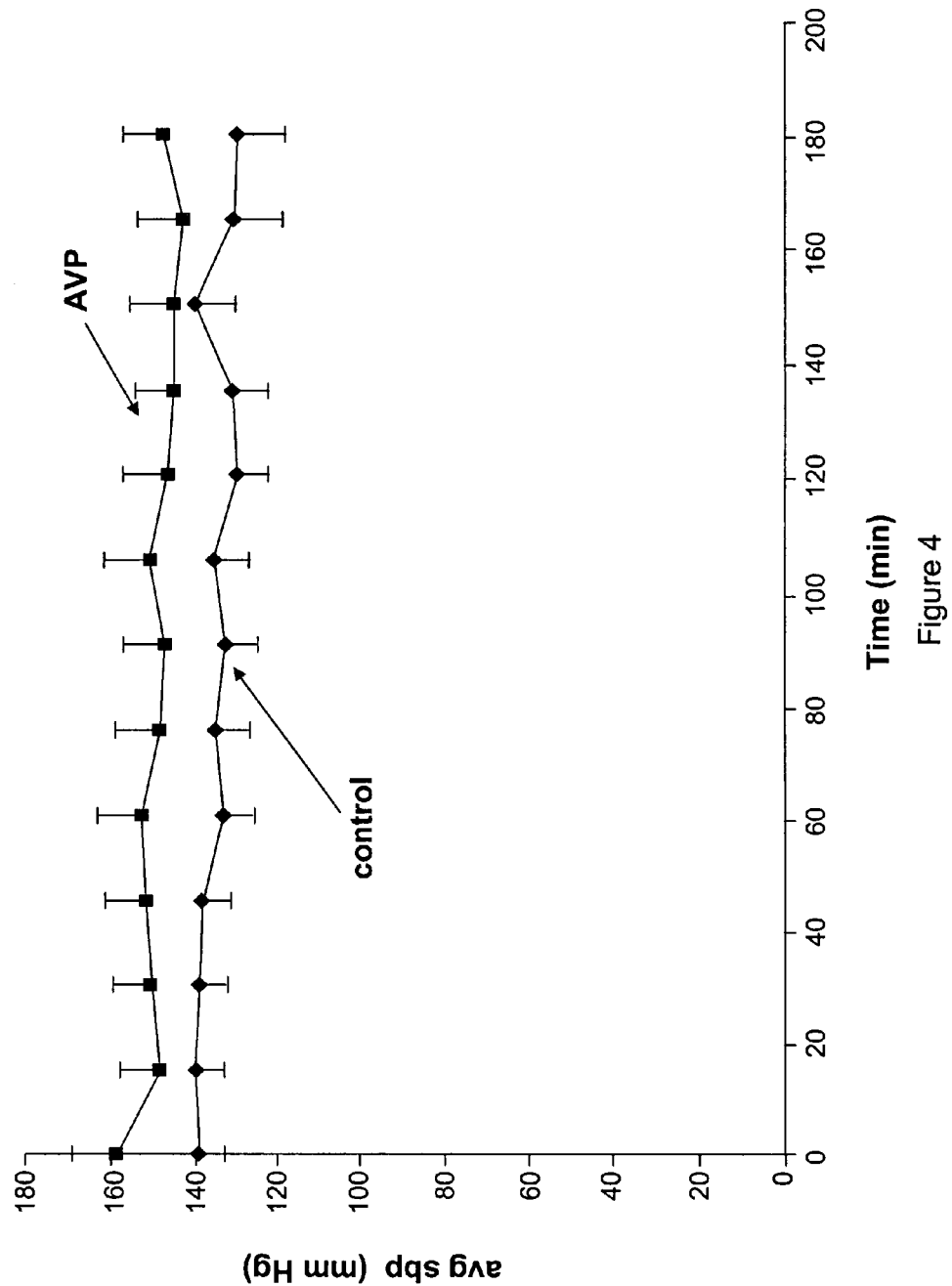
FIG. 4 depicts effect of AVP vs. placebo in subjects during hemodialysis.

AVP administration results in a higher intra-dialysis blood pressure. To examine whether vasopressin could help in supporting blood pressure during dialysis, we dialyzed a group of ESRD patients during administration of vehicle or during administration of vasopressin at a dose without pressor effect in normal subjects. Dialysis during administration of the hormone always resulted in a higher BP, thereby reducing the need to administer fluid to maintain pressure during dialysis (FIG. 4).

To determine the blood pressure effect of exogenous AVP during dialysis, two dialysis treatments were administered to twelve patients. In one, only the vehicle used to administer AVP was given while in the other treatment, AVP was infused. As shown, systolic arterial pressure decreased more than 10 mm Hg during the control dialysis while it decreased a maximum of 5 mm Hg during the dialysis in which AVP was infused.

|  | | Minutes of dialysis | | | | | |
| --- | --- | --- | --- | --- | --- | --- | --- |
| Dialysis | before | 30 | 60 | 90 | 120 | 150 | 180 |
| control | 144 ± 20 | 141 ± 20 | 132 ± 19 | 132 ± 22 | 131 ± 23 | 141 ± 25 | 132 ± 31 |
| AVP | 153 ± 28 | 153 ± 25 | 155 ± 29 | 149 ± 30 | 148 ± 30 | 149 ± 31 | 149 ± 30 | results are M ± SD. By ANOVA, the effect of AVP was highly significant (p < 0.005).

results are M±SD. By ANOVA, the effect of AVP was highly significant (p<0.005).

Figure 5:
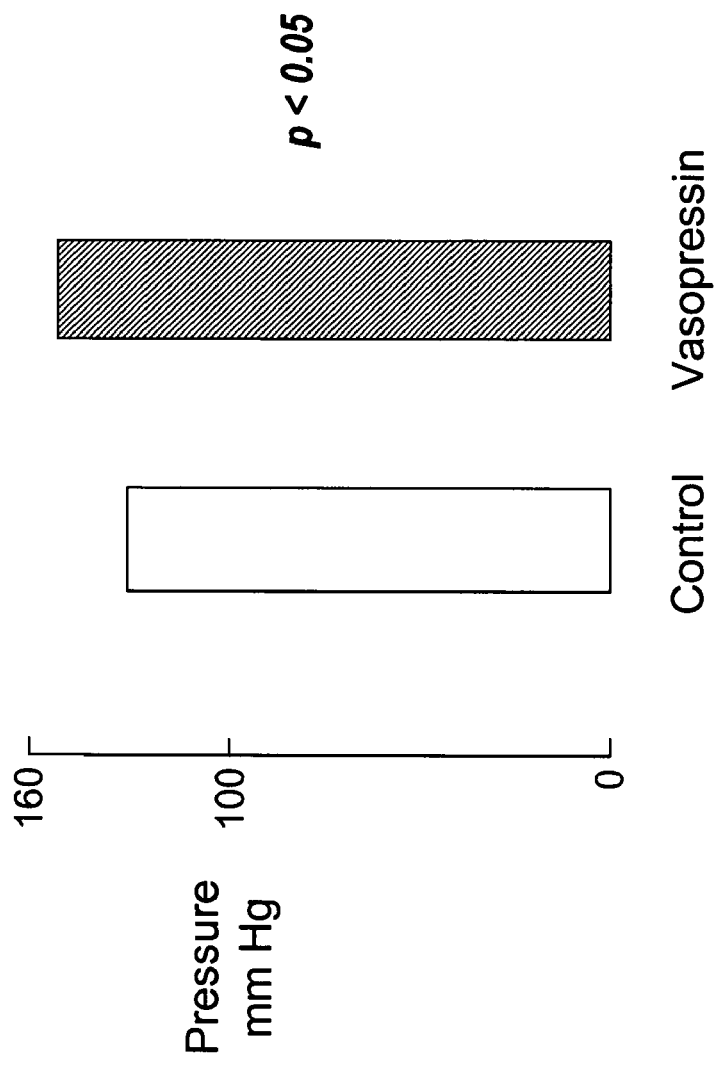
FIG. 5 depicts the effect of exogenous AVP on overall mean blood pressure during hemodialysis.

In summary, systolic arterial blood pressure is maintained at a higher level when AVP is administered during the hemodialysis (FIGS. 4 and 5).

AVP Administration allows more fluid removal. To determine whether the higher blood pressure during hemodialysis with AVP could resulted in a larger fluid removal, the amount of fluid needed to maintain blood pressure during dialysis and the amount of weight lost after was quantified in 5 patients during hemodialysis with AVP and without the hormone. Dialysis during the administration of AVP resulted both in a decreased in the amount of intravenous fluids needed to maintain blood pressure and in a greater decrease in weight.

The amount of fluids to maintain blood pressure during dialysis and the weight decrease were as given below:

|  | CONTROL | | AVP | |
| --- | --- | --- | --- | --- |
| Patient # | Fluids given, ml | Weight lost, Kg | Fluids given, ml | Weight lost, Kg |
| 1 | 300 ml | 2.2 | 0 | 2.8 |
| 2 | 300 ml | 1.7 | 0 | 1.8 |
| 3 | 650 ml | 0 | 0 | 2.2 |
| 4 | 200 ml | 2.8 | 0 | 3.0 |
| 5 | 0 | 2.0 | 0 | 2.2 |

As shown above and in FIG. 6, in all the patients on AVP, the blood pressure was stable and extra fluid removal was possible. However, in 4/5 of the control patients, extra fluid had to be administered.

In a similar study shown in FIG. 7, in the five patients on AVP, the blood pressure was stable and extra fluid removal was possible. However, two of the five patients receiving placebo had an episode of low blood pressure that prevented the removal of extra fluid.

In summary, patients with ESRD are unable to secrete the endogenous hormone during dialysis, are hypersensitive to exogenous vasopressin, and when vasopressin is administered during dialysis they maintain a higher and more constant pressure. This superior pressure control allows for a more effective volume removal during dialysis and favors a reduction in the hypertension of these patients.

Example 2

This Example describes a procedure to test that long term administration of vasopressin during hemodialysis results in an improvement of patient's hypertension.

Experimental Methods and Design

Data Collection

This is a randomized, double-blinded, placebo-controlled trial to determine the effect of AVP administration during dialysis on blood pressure.

Eligible patients are stratified for purposes of randomization into high blood pressure (systolic blood pressure or SBP 140-170) and very high blood pressure (SBP >170) groups, as well as diabetic and non-diabetic groups.

Patients are randomized to receive normal saline with AVP (treatment) or normal saline alone (placebo) during dialysis. A randomization protocol is used to determine whether the drug or placebo is to be administered. The identity of the substance being administered remains unknown to both the clinical staff and the patient. To insure that the nursing personnel does not become biased toward a particular group, all patients are introduced into the study by receiving 2 weeks of placebo solution, followed by 5 months of randomized treatment (AVP or placebo). To insure proper follow-up of all patients and to reinforce the blinding of the study, the protocol concludes with a 2-week placebo period for all patients.

The intervention in this study is to administer AVP at a rate of 0.3 mU/kg/min during consecutive dialysis sessions for 5 months. The outcome variables measured are the change in pre-dialysis blood pressure and, as well as left ventricular mass index, after the intervention.

The standard dialysis protocol is unaltered during the study except for the addition of an infusion of AVP through the venous limb of the dialysis circuit in the treatment group. Following routine, the sitting and standing blood pressures of each patient is measured before and after dialysis. Blood pressure and heart rate are recorded every 15 minutes by the dialysis machine. The volumes of fluid administered and removed per session are routinely recorded, as are the patient's pre- and post-dialysis weight. The procedure is followed for each dialysis session for a 5 month period. During the first month of the study and again 6 months later, a 2-dimensional transthoracic echocardiogram is performed and left ventricular mass index is calculated as a measure of left ventricular hypertrophy.

Since the placebo group in this experiment receive standard of care treatment, the placebo-control design is appropriate. The volume of AVP or placebo solution to be infused is generally be less than 200 ml, which contributes negligibly to any patient's fluid balance. Given the short half-life of AVP, no wash-in or wash-out periods are needed. Upon cessation of the study, all patients return to their standard dialysis treatment.

| Visit # | Procedure |
|---|---|
| 1–6 (Weeks 1–2) | Standard dialysis session with placebo |
| 6–66 (Weeks 3–22) | Dialysis session with AVP or placebo |
| 66–72 (Weeks 22–24) | Standard dialysis session with placebo |
| Month 1 | Echocardiogram |
| Month 6 | Echocardiogram |

*All visits are routine dialysis treatment sessions except the 2 echocardiogram sessions.

Analysis. The primary endpoint in this study is change in systolic blood pressure over the period of the intervention. Pre-dialysis blood pressure at a given time are defined as the mean value of the past 5 sessions, which will minimize the influence of session-to-session variability in measurement in our data analysis. Secondary endpoints are change in weight and change in degree of left ventricular hypertrophy.

Mean values for the outcome variables are calculated for the treatment and control treatment groups. The independent t test is used to distinguish effects attributable to AVP administration.

25 patients in each arm yield a power of 80% at the 0.05 significance level to detect a difference of 5 mm Hg in the blood pressure change between treatment and control groups. This sample size is derived in consultation with several biostatisticians, and takes into account the mortality rate of the population, as well as an inevitable dropout rate due to unforeseen circumstances. We do not expect to lose a significant number of patients to transplant since the average wait for a cadaveric kidney transplant in this group is 6 years.

Interpretation. If we demonstrate that administration of AVP during hemodialysis over a five-month period results in a sustained change in pre-dialysis blood pressure, we will conclude that, by using AVP to confer cardiovascular stability during the dialysis procedure we can improve hypertension, an important cause of morbidity and mortality in patients on hemodialysis.

If we demonstrate that changes in blood pressure are accompanied by change in left ventricular hypertrophy, we will conclude that our intervention is successful in treating not only hypertension itself but also one of its organ sequellae.

Example 3

Methods

Patients. Studies were performed at the Acute Dialysis Unit of the New York Presbyterian Hospital and at the Columbia University Dialysis Center, both located at Columbia Presbyterian Medical Center. All patients gave informed consent to participate in the study, which was approved by the Institutional Review Board of Columbia University.

All patients were studied at regularly scheduled dialysis sessions. Patients underwent conventional hemodialysis with hollow fiber high flux polysulfone dialyzers on volumetric dialysis machines (Cobe Centrysystem 3, Gambro Renal Care Products, Inc., Lakewood, Colo.). Dialysis times were 3.5–4.5 hours. Blood flow was 300–400 mL/min and dialysate was delivered at 600 mL/min. The dialysis bath contained potassium, 2 mEq/L; calcium, 2.5 mEq/L; magnesium, 0.75 mEq/L; and bicarbonate, 40 mEq/L. In those patients who were prescribed dialysate sodium modeling and/or reduced dialysate temperature (35–37° C.) prior to the study, the parameters of these interventions were held constant throughout the study. Ultrafiltration was performed at a constant rate based on the target weight loss for that dialysis session. Oscillometric blood pressure and heart rate measurements were taken at 15–30 minute intervals.

Exclusion criteria for all studies were: 1) active vascular disease, including angina, claudication, transient ischemic events, ischemic colitis and Raynaud's disease, 2) a history of prolonged QT syndrome, 3) a history of orthostatic hypotension and 4) a systolic blood pressure greater than 200 mm Hg and/or a diastolic blood pressure greater than 100 mm Hg. Fluid was administered for pressor support at the discretion of the dialysis staff, blinded to the study drug, on the basis of hypotensive episodes during dialysis. Excess fluid removed was defined as the difference between the baseline prescription weight loss and the actual weight loss achieved during the study hemodialysis.

Plasma vasopressin concentration. Vasopressin in plasma was determined as previously described (Landry, D. W., H. R. Levin, et al. (1997). *Circulation* 95(5): 1122–5).

Study Protocols

Administration of vasopressin. In eight normal subjects and eight patients with ESRD off dialysis, 8-arginine vasopressin (vasopressin, American Pharmaceutical Partners, Schaumberg, Ill.) in normal saline was administered through an antecubital intravenous line. In eight patients with ESRD during hemodialysis, vasopressin was infused through the venous (blood return) limb of the dialysis circuit throughout the dialysis session at a rate of 0.15 or 0.3 $mU \cdot kg^{-1} \cdot min^{-1}$.

Hemodialysis-induced fluid removal during vasopressin administration in hypertensive patients. 22 patients with ESRD on chronic hemodialysis and hypertension (defined by a systolic arterial pressure greater than 140 mm Hg or the requirement of anti-hypertensive medications to maintain a lower systolic arterial pressure) were studied. A randomized, controlled and double blinded trial compared the effect of vasopressin (0.3 $mU \cdot kg^{-1} \cdot min^{-1}$) or placebo (normal saline) on the capacity to tolerate a 0.5 kg increase in the target weight reduction specified by the standard dialysis prescription. Patients were studied only if their pre-dialysis weight was within ±1 kg. of the mean pre-dialysis weight of the previous three sessions.

Otherwise the hemodialysis routine was unchanged and its management was left to the health care personnel performing the treatment, who where not involved in the study. The nurse administering the hemodialysis treatment managed hypotensive episodes per routine with administration of normal saline and/or a decrease in ultrafiltration rate. Symptomatic hypotension was identified by the nurse conducting the dialysis and criteria included a sudden drop in systolic arterial pressure associated with one or more of the following: lightheadedness, dizziness, cramping, nausea and vomiting.

Statistical Analyses. Analyses were performed using Statistical Package for the Social Sciences, version 9. Changes in hemodynamic parameters within patients during each session and between sessions were analyzed by repeated measures of ANOVA. Analysis of continuous variables between treatment arms was performed using the Friedman (two-way) analysis of variance. All values are expressed as mean±SE unless otherwise stated. P values of less than 0.5 (two-tailed) were considered statistically significant.

Results

Effect of hemodialysis on the concentration of endogenous plasma vasopressin. Decreases in blood volume that activate the baroreflex trigger secretion of vasopressin, thereby increasing its plasma concentration (Dunn, F. L., T. J. Brennan, et al. (1973). *J Clin Invest* 52(12): 3212–9). To determine the effect of volume removal during hemodialysis on vasopressin release, plasma levels were determined in ten patients with ESRD during a standard hemodialysis treatment. The average weight of the patients before dialysis was 67±12 and decreased to 64±11 kg after treatment (p=0.01), a reduction of 4.5%. Plasma vasopressin concentration averaged 3.1±0.7 pg/ml before dialysis and 2.3±0.8 and 4.1±1.0 after one and two thirds of the procedure, respectively, and 5.0±1.5 pg/ml at its conclusion. Analysis of variance revealed that plasma vasopressin concentration was not significantly changed despite the decrease in body weight, as previously shown in hemodialysis (Horky, K., J. Sramkova, et al. (1979). *Horm Metab Res* 11(3): 241–6; Fasanella d'Amore, T., J. P. Wauters, et al. (1985). *Clin Nephrol* 23(6): 299–302; Hegbrant, J., H. Thysell, et al. (1993). *Nephron* 63(3): 303–8; Heintz, B., F. Konigs, et al. (1993). *Nephron* 65(2): 266–72; Heintz, B., K. Reiners, et al. (1993). *Clin Nephrol* 39(4): 198–204; Friess, U., W. Rascher, et al. (1995). *Nephrol Dial Transplant* 10(8): 1421–7; Uusimaa, P., K. Huttunen, et al. (1999). *Acta Physiol Scand* 165(1): 25–31) and in contrast to the increase in vasopressin observed in isolated ultrafiltration (Hegbrant, J., H. Thysell, et al. (1993). *Nephron* 63(3): 309–13; Ardaillou, R., W. Pruszczynski, et al. (1986). *Contrib Nephrol* 50: 46–53).

Figure 8:
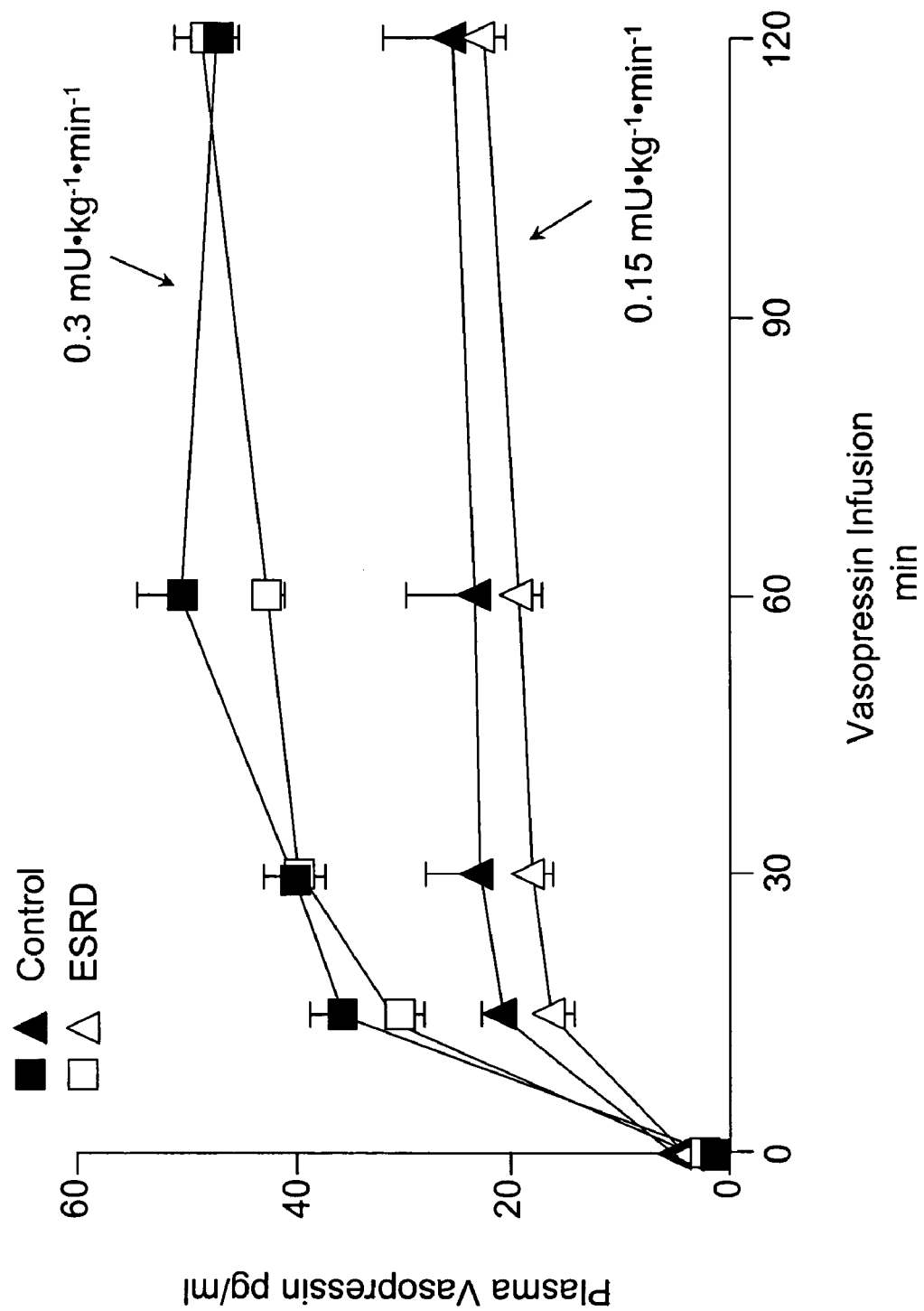
FIG. 8 depicts Plasma Vasopressin Concentration During Vasopressin Infusion.

Effect of vasopressin administration on its plasma concentration in normal subjects and Patients with ESRD. Because the effect of renal failure on the clearance of plasma vasopressin has remained unresolved (Shade, R. E. and L. Share (1976). *Endocrinology* 99(5): 1199–206; Benmansour, M., M. Rainfray, et al. (1982). *Eur J Clin Invest* 12(6): 475–80; Argent, N. B., R. Wilkinson, et al. (1992). *Clin Sci* (Lond) 83(5): 583–7), we administered a constant infusion of hormone to normal subjects and to patients with ESRD and measured plasma levels. Vasopressin was administered at doses (0.15 and 0.3 mU·kg$^{-1}$·min$^{-1}$) that do not increase arterial pressure in healthy subjects (Graybiel, A. and R. Glendy (1941). *American Heart Journal* 21: 481–489; Braunwald, E. and H. N. Wagner, Jr. (1956). *J Clin Invest* 35(12): 1412–8; Padfield, P. L., J. J. Brown, et al. (1976). *Lancet* 1(7972): 1255–7). FIG. 8 shows the resulting vasopressin concentrations at each infusion rate.

Final plasma concentrations were not significantly different between groups. Thus, renal failure does not alter the clearance of plasma vasopressin. The two doses of vasopressin increased plasma levels to ~20 pg/ml and ~45 pg/ml, respectively, values seen during modest hemorrhage (Weitzman, R. E., A. Reviczky, et al. (1980). *Am J Physiol* 238(1): E62–8; Matsui, K., L. Share, et al. (1983). *Endocrinology* 112(6): 2114–9) or hypotension (Minaker, K. L., G. S. Meneilly, et al. (1991). *J Gerontol* 46(4): M151–4). It should be noted that while these plasma concentrations do not increase arterial pressure in healthy subjects (Graybiel, A. and R. Glendy (1941). *American Heart Journal* 21: 481–489; Braunwald, E. and H. N. Wagner, Jr. (1956). *J Clin Invest* 35(12): 1412–8; Padfield, P. L., J. J. Brown, et al. (1976). *Lancet* 1(7972): 1255–7), identical levels do have vascular action when arterial pressure is threatened (Landry, D. W., H. R. Levin, et al. (1997). *Circulation* 95(5): 1122–5; Aisenbrey, G. A., W. A. Handelman, et al. (1981). J Clin Invest 67(4): 961–8).

Effect of hemodialysis on plasma vasopressin concentration during constant infusion of hormone. To determine whether hemodialysis removes vasopressin from plasma (Shimamoto, K., T. Ando, et al. (1977). *J Clin Endocrinol Metab* 45(4): 818–20; Rosansky, S. J., R. Rhinehart, et al. (1991). *Clin Nephrol* 35(4): 158–64), we examined the effect of the procedure on the steady state plasma concentration of hormone during constant infusion. Vasopressin was infused for >1 hour to obtain a stable plasma concentration, at which time hemodialysis was initiated. Table 1 shows that plasma concentrations of vasopressin were not significantly changed by hemodialysis, indicating that vasopressin in plasma is not cleared by dialysis.

TABLE 1

Effect of Hemodialysis on Plasma Vasopressin during Vasopressin Infusion.

| Vasopressin Infusion | Plasma Vasopressin pg · ml − 1 | | |
|---|---|---|---|
| | Start Dialysis | 1 h Dialysis | 2 h Dialysis |
| 0.15 mU · kg$^{-1}$ · min$^{-1}$ | 26 ± 4 | 25 ± 6 | 29 ± 6 |
| 0.3 mU · kg$^{-1}$ · min$^{-1}$ | 47 ± 6 | 54 ± 6 | 52 ± 9 |

Figure 9:
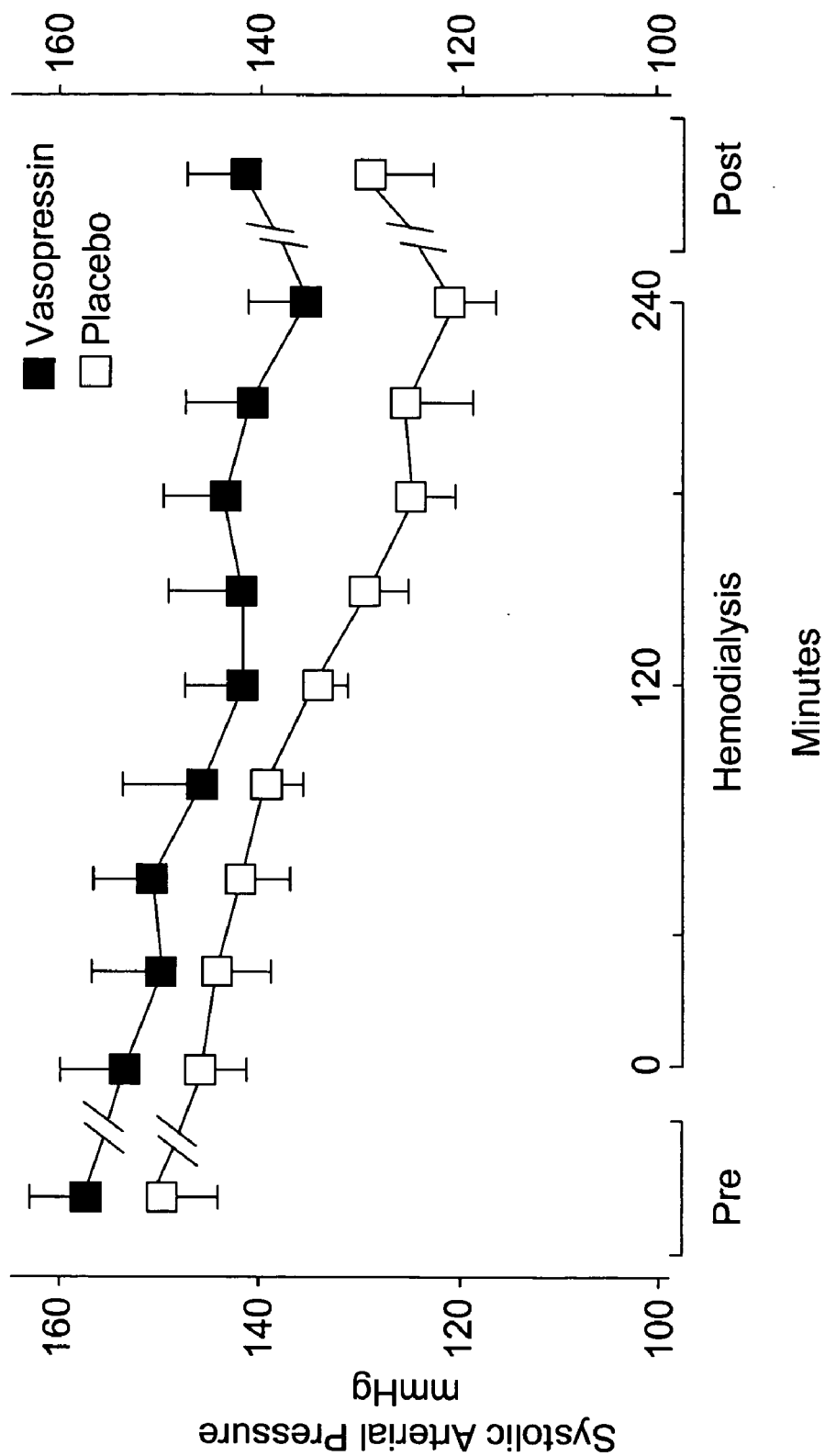
FIG. 9 depicts Blood Pressure Profile During Study Hemodialysis.

Effect of vasopressin administration during increased hemodialysis-induced luid removal. To test the hypothesis that exogenous vasopressin improves blood pressure stability during hemodialysis-mediated fluid removal, the target for weight reduction in a dialysis session was increased by 0.5 kg beyond the baseline prescription to "remove the weight gained since the last treatment." Because hypertension in patients with ESRD is largely due to expansion of the extracellular fluid volume (Blumberg, A., W. B. Nelp, et al. (1967). *Lancet* 2(7506): 69–73; Vertes, V., J. L. Cangiano, et al. (1969). *N Engl J Med* 280(18): 978–81) patients with hypertension between dialysis treatments were selected for this study. On the day of study, subjects were randomized to receive, in double blinded fashion, placebo or vasopressin (0.3 mU·kg$^{-1}$·min$^{-1}$) during the dialysis. Table 2 shows the patient characteristics and important parameters of the dialysis session and FIG. 9 shows the systolic arterial pressure of the two groups during dialysis.

TABLE 2

Patient Characteristics and Hemodialysis Parameters on Day of Study.

| | Placebo | Vasopressin | P |
|---|---|---|---|
| Patient Characteristics | | | |
| Age (years) | 60.8 ± 2.0 | 55.2 ± 2.8 | 0.54 |
| Gender (female:male) | 1:10 | 2:9 | 0.23 |
| Diabetes (%) | 64 ± 1.5 | 36 ± 1.5 | 0.56 |
| Number of antihypertensive medications per patient | 2.5 ± 0.3 | 2.3 ± 0.4 | 0.50 |
| Mean fluid loss* during previous sessions (kg) | 3.1 ± 0.3 | 3.3 ± 0.4 | 0.72 |
| Hemodialysis Parameters on Day of Study | | | |
| Baseline prescribed fluid loss† (kg) | 2.9 ± 0.3 | 2.7 ± 0.4 | 0.74 |
| Study target fluid loss (kg) | 3.4 ± 0.3 | 3.2 ± 0.4 | 0.71 |
| Mean SAP during dialysis (mmHg) | 136 ± 4 | 145 ± 6 | 0.19 |
| Maximum drop in SAP from mean (mmHg) | 34 ± 5 | 17 ± 2 | 0.03 |

TABLE 2-continued

Patient Characteristics and Hemodialysis Parameters on Day of Study.

| | Placebo | Vasopressin | P |
|---|---|---|---|
| Lowest SAP (mmHg) | 114 ± 5 | 130 ± 7 | 0.02 |
| Symptomatic hypotensive episodes (%) | 73 ± 1% | 9 ± 1% | 0.001 |

*Fluid loss was defined as the difference between the patient's pre- and post-dialysis weights. The mean value of the previous 3 dialyses is shown.
†Baseline prescribed fluid loss was determined by the difference between the patient's pre-dialysis weight and his or her usually prescribed dry weight.

The weight gained since the last treatment (baseline prescription) and, therefore, the "Study target fluid loss" (baseline prescription plus 0.5 kg) did not differ between the two groups. Similarly, systolic arterial pressures before, during and after the dialysis were not significantly different between the two groups. However, systolic arterial pressure in the group of patients that received vasopressin was significantly more stable during the dialysis. In this group, when compared to the placebo group, the maximum drop from the overall systolic pressure was smaller (17±2 vs. 34±5 mm Hg, p=0.03) and the lowest systolic pressure was higher (130±7 vs. 114±5, p=0.02), indicating that vasopressin participated in arterial pressure maintenance as fluid was removed. In addition, increasing the target volume for fluid removal resulted in symptomatic hypotensive episodes in seven of the eleven patients receiving placebo but only one patient of eleven patients receiving vasopressin (63% vs. 9%, p=0.001).

Figure 10:
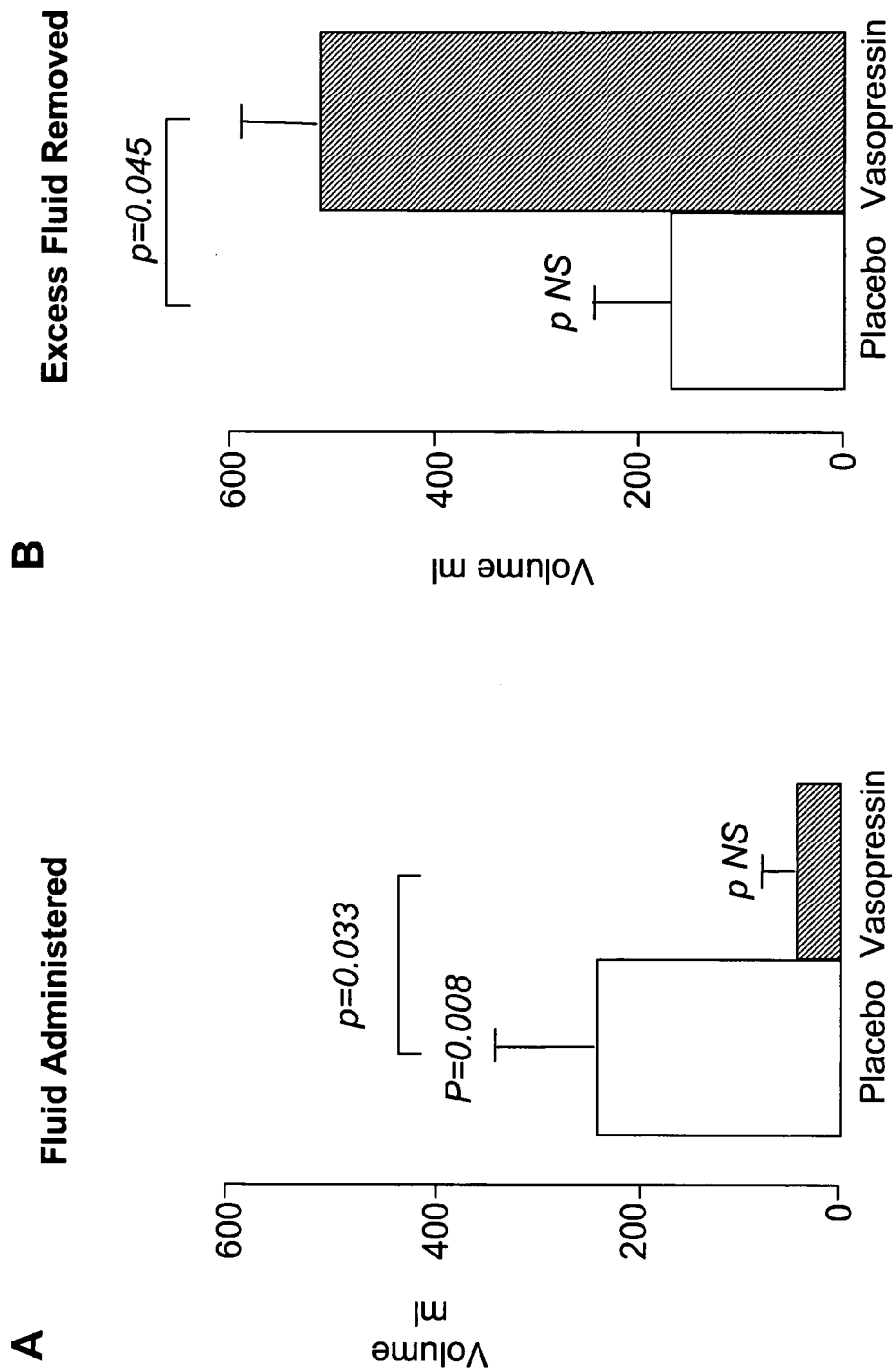
FIG. 10 depicts Volume Administered for Pressor Support and Excess Fluid Removed during Study Hemodialysis.

In response to arterial pressure changes during dialysis, the nurse conducting the dialysis administered to patients in the placebo group 245±74 ml of normal saline for pressure support (p=0.008) but a non-significant amount of saline to those receiving vasopressin (40±43 ml; p=0.03 vs placebo; FIG. 10A).

Finally, while the volume of extra fluid removed during the dialysis above the baseline prescription was not significant in the placebo group, (170±130 ml), patients receiving vasopressin attained the study's goal for additional fluid removal (460±100 ml; p<0.001; p=0.045 vs. placebo; FIG. 10B). After the hemodialysis session, all patients were managed per routine. No patient reported orthostatic symptoms between the end of the study and the following dialysis.

Discussion

During hemodialysis, excess extracellular fluid is removed by ultrafiltration until the patient is returned to his or her "dry weight." However, "dry weight" is empirically assigned to that weight at which symptomatic decreases in blood pressure are very likely to occur if further volume is removed (Henderson, L. W. (1980). *Kidney Int* 17(5): 571–6; Jaeger, J. Q. and R. L. Mehta (1999). *J Am Soc Nephrol* 10(2): 392–403; Fisch, B. J. and D. M. Spiegel (1996). *Kidney Int* 49(4): 1105–9; Leypoldt, J. K., A. K. Cheung, et al. (2002). *Kidney Int* 61(1): 266–75). Even in the presence of expanded extracellular fluid volume (i.e., edema), fluid removal by hemodialysis frequently causes hypotension, a complication that has beleaguered hemodialysis therapy since its inception. Thus, to avoid hypotension during hemodialysis a paradox results in that patients at their "dry weight" are often extracellularly volume expanded (Fisch, B. J. and D. M. Spiegel (1996). *Kidney Int* 49(4): 1105–9; Katzarski, K. S., J. Nisell, et al. (1997). *Am J Kidney Dis* 30(4): 459–65; Spiegel, D. M., K. Bashir, et al. (2000). *Clin Nephrol* 53(2): 108–14) and consequently hypertensive between dialysis treatments (Blumberg, A., W. B. Nelp, et al. (1967). *Lancet* 2(7506): 69–73; Vertes, V., J. L. Cangiano, et al. (1969). *N Engl J Med* 280(18): 978–81; Mailloux, L. U. and W. E. Haley (1998). *Am J Kidney Dis* 32(5): 705–19).

Reduction of extracellular fluid volume during hemodialysis often fails to elicit the systemic vasoconstriction (Endou, K., J. Kamijima, et al. (1978). *Cardiology* 63(3): 175–87; Rouby, J. J., J. Rottembourg, et al. (1980). *Kidney Int* 17(6): 801–10; Baldamus, C. A., W. Ernst, et al. (1982). *Nephron* 31(4): 324–32; Santoro, A., E. Mancini, et al. (1990). *Nephrol Dial Transplant* 5 Suppl 1: 147–53; Converse, R. L., Jr., T. N. Jacobsen, et al. (1992). *J Clin Invest* 90(5): 1657–65) that normally occurs when fluid is removed by ultrafiltration without hemodialysis (Rouby, J. J., J. Rottembourg, et al. (1980). *Kidney Int* 17(6): 801–10; Baldamus, C. A., W. Ernst, et al. (1982). *Nephron* 31(4): 324–32). We recently found that an important pathogenetic factor in some forms of hypotension without vasoconstriction is an inappropriately low concentration of plasma vasopressin (reviewed in Landry, D. W. and J. A. Oliver (2001). *N Engl J Med* 345(8): 588–95.) In addition to osmolarity, the secretion of vasopressin is under baroreflex control and the hormone contributes to blood pressure maintenance during decreases in blood volume or cardiac output (Dunn, F. L., T. J. Brennan, et al. (1973). *J Clin Invest* 52(12): 3212–9; Aisenbrey, G. A., W. A. Handelman, et al. (1981). *J Clin Invest* 67(4): 961–8). During a standard hemodialysis treatment, plasma volume typically decreases about 10 to 20% (Uusimaa, P., K. Huttunen, et al. (1999). *Acta Physiol Scand* 165(1): 25–31; Heintz, B., K. Reiners, et al. (1993). *Clin Nephrol* 39(4): 198–204; Leypoldt, J. K., A. K. Cheung, et al. (2002). *Kidney Int* 61(1): 266–75), a change that is in itself sufficient to induce vasopressin secretion (Dunn, F. L., T. J. Brennan, et al. (1973). *J Clin Invest* 52(12): 3212–9) and that indeed increases plasma vasopressin in patients with ESRD when fluid is removed by isolated ultrafiltration (Hegbrant, J., H. Thysell, et al. (1993). *Nephron* 63(3): 309–13; Ardaillou, R., W. Pruszczynski, et al. (1986). *Contrib Nephrol* 50: 46–53). However, we found that plasma vasopressin does not increase when extracellular fluid is removed during hemodialysis, confirming the observations of others (Horky, K., J. Sramkova, et al. (1979). *Horm Metab Res* 11(3): 241–6; Fasanella d'Amore, T., J. P. Wauters, et al. (1985). *Clin Nephrol* 23(6): 299–302; Hegbrant, J., H. Thysell, et al. (1993). *Nephron* 63(3): 303–8; Heintz, B., F. Konigs, et al. (1993). *Nephron* 65(2): 266–72; Heintz, B., K. Reiners, et al. (1993). *Clin Nephrol* 39(4): 198–204; Friess, U., W. Rascher, et al. (1995). *Nephrol Dial Transplant* 10(8): 1421–7; Uusimaa, P., K. Huttunen, et al. (1999). *Acta Physiol Scand* 165(1): 25–31) (although rare exceptions have been reported (Nakayama, M., K. Yamada, et al. (1998). *Nephron* 79(4): 488–9). We demonstrated that the failure of plasma vasopressin to increase is not due to loss of hormone through the dialysis membrane nor to increased catabolism of the hormone in ESRD patients; thus it is clear that extracellular fluid removal during hemodialysis fails to induce appropriate vasopressin secretion.

To test whether the inability to secrete vasopressin is a pathogenetic factor in the blood pressure instability associated with hemodialysis, we administered the hormone to achieve plasma levels that have no pressor effect in controls (Graybiel, A. and R. Glendy (1941). *American Heart Journal* 21: 481–489; Braunwald, E. and H. N. Wagner, Jr. (1956). *J Clin Invest* 35(12): 1412–8; Padfield, P. L., J. J.

Brown, et al. (1976). *Lancet* 1(7972): 1255–7) but are seen during modest volume depletion or hypotension (Weitzman, R. E., A. Reviczky, et al. (1980). *Am J Physiol* 238(1): E62–8; Matsui, K., L. Share, et al. (1983). *Endocrinology* 112(6): 2114–9; Minaker, K. L., G. S. Meneilly, et al. (1991). *J Gerontol* 46(4): M151–4; Aisenbrey, G. A., W. A. Handelman, et al. (1981). *J Clin Invest* 67(4): 961–8). We found that when the amount of extracellular fluid to be removed by hemodialysis was substantial increased (17%) above the baseline prescription, vasopressin administration markedly improved the stability of the systolic arterial pressure, indicating that the hormone is required to maintain blood pressure as extracellular fluid volume is decreased by dialysis.

Taken together, our results indicate that the failure to secrete vasopressin contributes to the cardiovascular instability that complicates hemodialysis. These observations suggest that dialysis hypotension, like other states of vasodilatory hypotension, is characterized by a deficiency of vasopressin and exquisite sensitivity to replacement of exogenous hormone (Landry, D. W. and J. A. Oliver (2001). *N Engl J Med* 345(8): 588–95).[41]

There is a pressing need to improve the treatment of hypertension in patients with ESRD, who are at high risk for cardiovascular events and have a markedly reduced life span (Mailloux, L. U. and W. E. Haley (1998). *Am J Kidney Dis* 32(5): 705–19; Foley, R. N., P. S. Parfrey, et al. (1996). *Kidney Int* 49(5): 1379–85). Recent studies in patients with ESRD suggest that decreasing the rate of fluid removal by extending hemodialysis improves hemodynamic stability and ameliorates chronic hypertension, likely because extracellular fluid volume is better controlled (Charra, B., E. Calemard, et al. (1983). *Nephron* 33(2): 96–9; Pierratos, A., M. Ouwendyk, et al. (1998). *J Am Soc Nehrol* 9(5): 859–68). Replacement with non-pressor doses of vasopressin during hemodialysis may provide an additional therapeutic tool to attain this goal.

Various publications are cited herein that are hereby incorporated by reference in their entirety.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

What is claimed is:

1. A method for reducing excess extracellular fluid in a hypertensive subject undergoing hemodialysis comprising administering a vasopressin (V-1) receptor agonist to the subject in an effective amount and thereby maintaining blood pressure during hemodialysis in order to facilitate reducing excess extracellular fluid in the subject.

2. A method for stabilizing high blood pressure between hemodialysis treatments in a hypertensive subject undergoing hemodialysis by reducing excess extracellular fluid by the method of claim 1.

3. A method for inhibiting interdialytic hypertension by regulating blood pressure by the method of claim 2.

4. A method for inhibiting intradialytic hypotension by regulating blood pressure by the method of claim 1.

5. The method of claim 1, wherein the V-1 receptor agonist is arginine vasopressin.

6. The method of claim 1, wherein the V-1 receptor agonist is lysine vasopressin.

7. The method of claim 1, wherein the V-1 receptor agonist is terlipressin.

8. The method of claim 1, wherein the V-1 receptor agonist is octapressin.

9. The method of claim 1, wherein the V-1 receptor agonist is omipressin.

10. The method of claim 1, wherein the V-1 receptor agonist is an organic molecule selected from the group consisting of 3-beta-(2-thienyl)-L-alanine)-8-lysine-vasopressin, N-alpha-glycyl-glycyl-glycyl-[8-lysine]-vasopressin, and 1-deamino-6-carba-[8-arginine]-vasopressin.

11. The method of claim 1, wherein the effective amount of the V-1 receptor agonist is in a range of about 0.05 milliunits/kg/minute—2.0 milliunits/kg/hr.

12. The method of claim 1, wherein the effective amount of the V-1 receptor agonist is about 0.3 milliunits/kg/minute.

13. The method of claim 1, wherein the subject is a human, non-human primate, rabbit, sheep, rat, dog, cat, pig, or mouse.

* * * * *